(12) United States Patent
Kobayashi et al.

(10) Patent No.: US 8,499,924 B2
(45) Date of Patent: Aug. 6, 2013

(54) CHIP COMPONENT CARRYING METHOD AND SYSTEM, AND VISUAL INSPECTION METHOD AND SYSTEM

(75) Inventors: Masayoshi Kobayashi, Tokyo (JP); Toru Mizuno, Tokyo (JP)

(73) Assignee: TDK Corporation, Tokyo (JP)

(*) Notice: Subject to any disclaimer, the term of this patent is extended or adjusted under 35 U.S.C. 154(b) by 0 days.

(21) Appl. No.: 13/174,001

(22) Filed: Jun. 30, 2011

(65) Prior Publication Data

US 2011/0261185 A1 Oct. 27, 2011

Related U.S. Application Data

(62) Division of application No. 11/578,062, filed as application No. PCT/JP2004/013284 on Sep. 7, 2004, now Pat. No. 7,987,968.

(30) Foreign Application Priority Data

Apr. 13, 2004 (JP) .................................. 2004-117651

(51) Int. Cl.
*B65G 29/00* (2006.01)

(52) U.S. Cl.
USPC .............. 198/689.1; 198/397.03; 198/397.04; 198/397.05

(58) Field of Classification Search
None
See application file for complete search history.

(56) References Cited

U.S. PATENT DOCUMENTS

| 4,074,654 A | 2/1978 | Noguchi et al. |
| 4,353,456 A | 10/1982 | Yamamoto |
| 4,757,382 A * | 7/1988 | Kaziura et al. .................. 348/92 |
| 5,746,323 A | 5/1998 | Dragotta |
| 5,826,696 A | 10/1998 | Rupp et al. |
| 6,741,731 B1 * | 5/2004 | Yamamoto et al. ........... 382/141 |

FOREIGN PATENT DOCUMENTS

| JP | 62-136281 | 6/1987 |
| JP | 03-042415 | 2/1991 |
| JP | 6-54226 | 7/1994 |
| JP | 6-286856 | 10/1994 |
| JP | 6-87072 | 11/1994 |
| JP | 08-075667 | 3/1996 |
| JP | 08-247740 | 9/1996 |

(Continued)

OTHER PUBLICATIONS

Office Action issued Sep. 3, 2008, in Japanese Patent Application No. 2004-117651 (with English-Language Translation).

*Primary Examiner* — Kavel Singh
(74) *Attorney, Agent, or Firm* — Oblon, Spivak, McClelland, Maier & Neustadt, L.L.P.

(57) ABSTRACT

A method and a system for stabilizing the sight line of a chip component being carried on two discs, for stabilizing delivery of the chip component between the two discs, and improving and stabilizing the inspection accuracy in the visual check of the chip component. This is achieved by employing a mechanism for carrying the chip component while supporting it on the horizontal plane of the first rotary disc and then carrying the chip component while suction-holding it on the vertical plane of the second rotary disc. When the chip component is carried on the first rotary disc, the upper surface and one side face of the chip component are imaged by first and second cameras. When the chip component is carried on the second rotary disc, the lower surface and the other side face of the chip component are imaged by third and fourth cameras.

9 Claims, 18 Drawing Sheets

(56) References Cited

FOREIGN PATENT DOCUMENTS

| | | |
|---|---|---|
| JP | 2585133 | 11/1996 |
| JP | 2000-203713 | 7/2000 |
| JP | 2000-266521 | 9/2000 |
| JP | 2000-337843 | 12/2000 |
| JP | 2001-031241 | 2/2001 |
| JP | 2002-68470 | 3/2002 |
| JP | 2002068470 A * | 3/2002 |
| JP | 2002-193440 | 7/2002 |
| JP | 2002-286646 | 10/2002 |
| JP | 2003-341832 | 12/2003 |

* cited by examiner

ENLARGEMENT OF X AREA

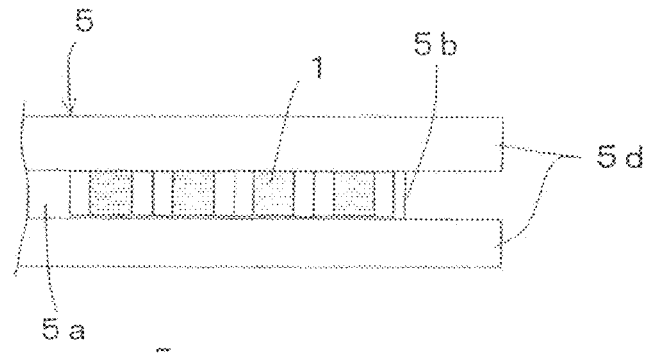
FIG. 11A
FIG. 11B
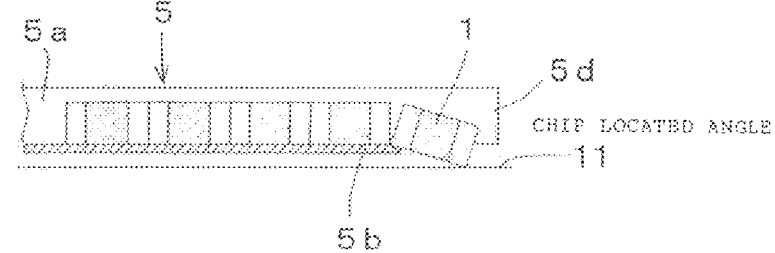
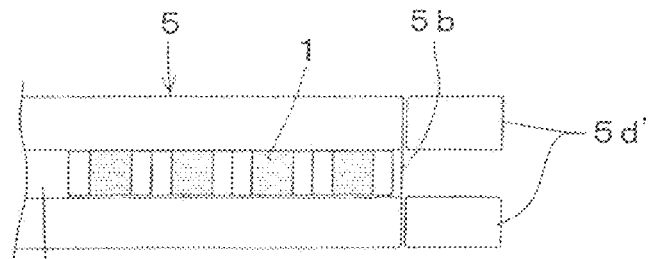
FIG. 12A
FIG. 12B
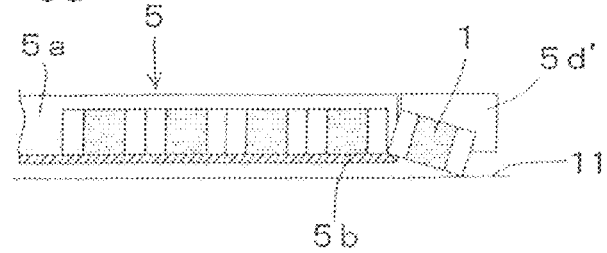

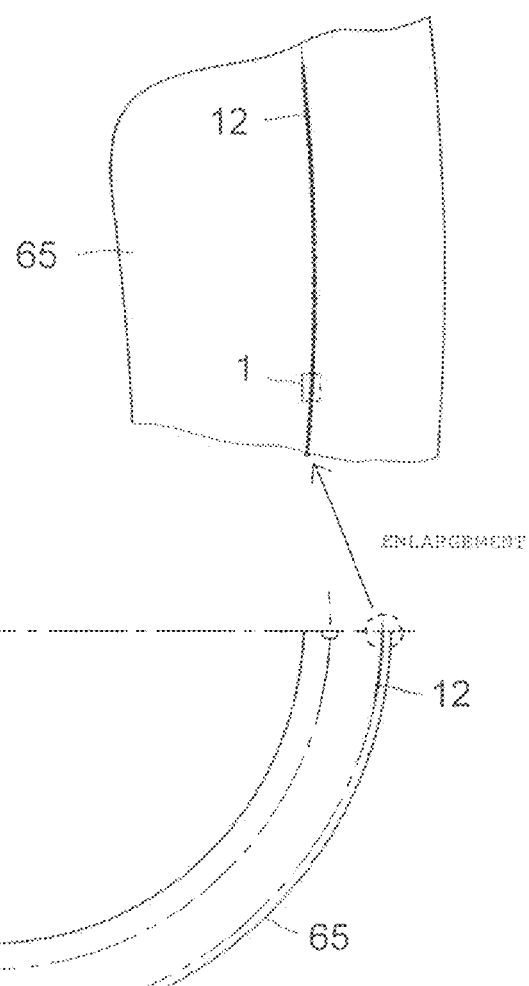
FIG. 14A
FIG. 14B
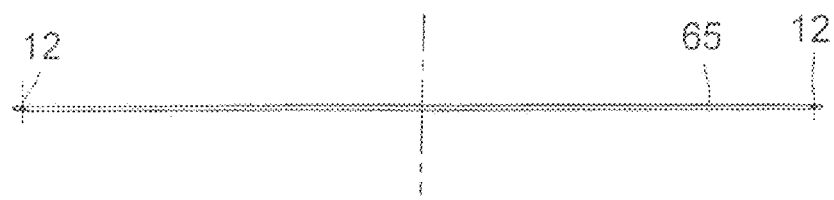

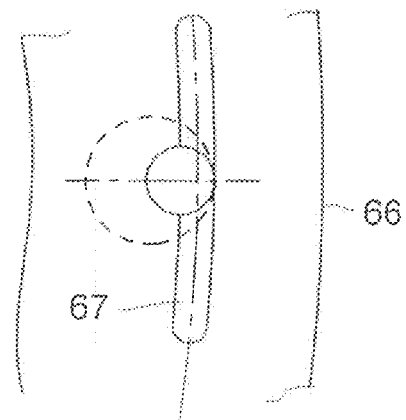
FIG. 15A
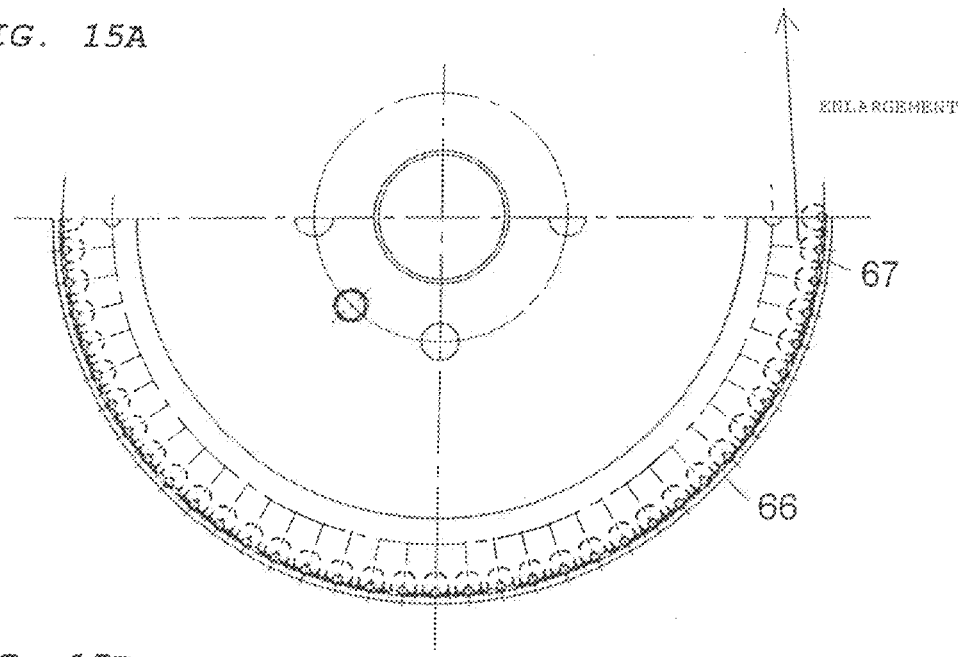
FIG. 15B
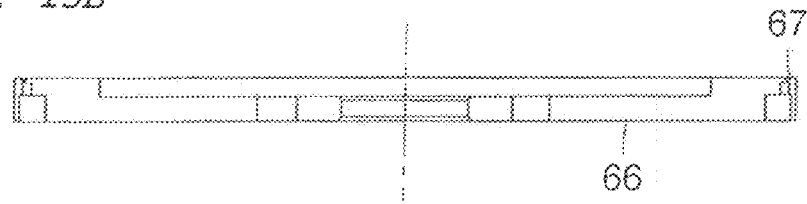

CHIP COMPONENT CARRYING METHOD AND SYSTEM, AND VISUAL INSPECTION METHOD AND SYSTEM

CROSS-REFERENCE TO PRIORITY APPLICATIONS

The present patent document is a divisional of U.S. application Ser. No. 11/578,062 filed on Oct. 12, 2006, which is based on PCT/JP2004/013284 filed on Sep. 7, 2004, and claims priority to JP 2004-117651 filed on Apr. 13, 2004, the entire contents of each of which are hereby incorporated herein by reference.

TECHNICAL FIELD

The present invention relates to a chip-component carrying method and system suitable to image four faces (upper face, lower face, and both side faces other than both end faces) of a chip component such as a chip condenser or chip inductor and a visual inspection method and system using the carrying method and system.

BACKGROUND ART

The following are carrying techniques for transferring a chip component such as a chip condenser or chip inductor for inspection.

(1) Technique for forming a workpiece housing groove on a rotary disc, supplying a workpiece (object to be carried) to the workpiece housing groove, and separation-carrying the workpiece in accordance with an intermittent action (commercial inspection machine)

(2) Technique for separation-supplying a workpiece to a continuously-rotating rotary disc from a part feeder as disclosed in Japanese Patent Laid-Open No. 2000-266521 or Japanese Patent Publication No. H6-87072 and then carrying the workpiece supplied onto the rotating rotary disc by only dead weight (3) Technique for separation-supplying a workpiece onto a continuously-carried belt as disclosed in Japanese Patent Laid-Open No. 2000-337843

Patent Document 1: Japanese Patent Laid-Open No. 2000-266521

Patent Document 2: Japanese Patent Publication No. H6-87072

Patent Document 3: Japanese Patent Laid-Open No. 2000-337843

Moreover, as a conventional technique for a workpiece-sides (four sides) inspection method, there is a method for inspecting the upside, laterals, and downside of a workpiece on a rotary disc. For example, as disclosed in Japanese Patent Publication No. H6-54226, there is a configuration using a two-side inspection instrument for a chipped component. In this case, there are the following configurations: a configuration in which a rotor plate is transparent and a configuration for delivering a workpiece.

(1) Configuration in which a rotor plate is constituted of a transparent member (e.g.: hard glass) and upside and both laterals of workpiece are inspected by three CCD cameras disposed on to recognize the downside from through a transparent rotor plate (2) Configuration in which two sides (upside and one of laterals) or three sides (upside and both laterals) of a workpiece present on a rotary disc are inspected and the workpiece is delivered to the next rotary disc to inspect the remaining two sides (downside and the other of the laterals) or one side (downside)

Moreover, as a technique for improving a suction plate structure of a rotary disc for sucking and carrying a workpiece, a configuration disclosed in, for example, Japanese Patent Laid-Open No. 2001-31241 is known.

Patent Document 5: Japanese Patent Laid-Open No. 2001-31241

Because a workpiece suction hole is formed in the case of this configuration, it is necessary to form a suction hole by laminating at least cover plate portions at the upside and downside of a plate portion on which a slit for suction is formed and in this case, three or four component members are necessary.

FIGS. 6 and 7 show a conventional chip-component carrying apparatus and show a configuration for delivering a chip component 1 as a workpiece by two rotary discs. This apparatus is provided with a part feeder 50, lower rotary disc 51, and upper rotary disc 52, in which a plurality of suction holes 53 are formed on the downside of the upper rotary disc 52. A workpiece carried on the continuously-rotating lower rotary disc 51 is sucked by the suction hole 53 at the continuously-rotating upper rotary disc-52 side to deliver the chip component 1.

When performing a visual inspection of a chip component by using the chip-component carrying apparatus, the upside and one lateral of the chip component being carried by the lower rotary disc 51 are imaged by imaging means and downside and the other lateral of the chip component being carried by the upper rotary disc 52 are imaged by the imaging means. Thereby, four-side inspection of the chip component is realized.

The following are problems of a conventional carrying technique.

(1) In the case of a workpiece carrying method, the attitude of a workpiece is not stabilized due to the influence of acceleration or deceleration when carrying the workpiece by intermittent driving. Moreover, there is a problem that a throughput cannot be earned.

(2) When carrying a workpiece by continuous rotary discs, because the workpiece is carried by the dead weight of the workpiece, an incorrect workpiece attitude occurs by the influence of a shift of the workpiece due to centrifugal force caused by rise of a carrying speed or mechanical vibration due to a change of equipment to high speed. When the state of a detection face is fluctuated due to the incorrect attitude of the workpiece, a trouble occurs in visual inspection accuracy (recognition accuracy).

(3) When carrying a workpiece by belts, similarly there is a problem that an attitude of the workpiece is fluctuated due to a vibration of the belt itself.

Moreover, the following are problems of a conventional inspection method.

(1) In the case of a detection method of four sides of a workpiece using a transparent member, though a carrying method is simple because no workpiece is delivered, dirt and scratch easily occur on the transparent member and these dirt and scratch cause a problem in an inspection accuracy and there is a problem in stable detection (originally nondefective product is confused as defective product).

(2) In the case of the conventional workpiece delivery using two rotary discs shown in FIGS. 6 and 7, a workpiece carried on the continuously-rotating lower rotary disc 51 is sucked by the suction hole 53 at the continuously-rotating upper rotary disc-52 side to deliver the workpiece. In the case of this method, however, there are problems that the gap between the workpiece and the upper rotary disc 52 is influenced by the dimensional tolerance of the thickness of the workpiece, clearance control is difficult, and delivery of the workpiece is not well-performed when the gap is too large. Moreover, there is a problem that a trouble that a workpiece having an incorrect workpiece attitude is caught in the gap between the upper and lower rotary discs easily occurs.

Furthermore, there is Patent Document 5 as a suction plate structure when sucking the lateral of a workpiece. Because a workpiece suction hole is formed in the case of the technique disclosed in Patent Document 5, it is necessary to form a suction hole by laminating at least cover plate portions at the top and bottom of a plate portion on which a slit for suction is formed. In this case, three or four component members are necessary and there is a problem that a structure becomes complicated. The disclosed content of the above-described Japanese Patent Laid-Open No. 2001-31241 does not refer to the four-side inspection of a workpiece due to delivery.

DISCLOSURE OF THE INVENTION

The first object of the present invention is to provide a chip-component carrying method and a chip-component carrying system for carrying a workpiece (chip component) while the attitude of the workpiece is stabilized by first and second rotary discs and stabilizing the delivery operation by improving the delivery of the workpiece between the first and second rotary discs and thereby, stabilizing a series of workpiece carryings by the first and second rotary discs in view of the above point.

The second object of the present invention is to carry a chip component by using the above chip-component carrying method and system and provide a chip-component visual inspection method and system for improving and stabilizing the inspection accuracy of the visual inspection of a chip component.

Other object and new feature of the present invention will become more apparent from the embodiment to be described later.

To achieve the above objects, a chip component carrying method of the present invention is characterized by supporting a chip component by a first rotary disc on a horizontal plane and carrying the chip component and then suction-holding the chip component on the vertical plane of a second rotary disc and carrying the component.

Moreover, a chip-component carrying method of the present invention is characterized in that the first rotary disc and the second rotary disc are continuously rotating in the above configuration.

Moreover, to achieve the above objects, a chip-component carrying system of the present invention is characterized by including a first rotary disc for carrying a chip component by supporting the chip component on a horizontal plane and a second rotary disc for suction-holding the chip component on the first rotary disc on a vertical plane and carrying the chip component.

In the case of a chip-component carrying system of the present invention, the second rotary disc has a plate portion provided with a groove on which a suction groove is formed through half etching and a cover plate portion using the suction groove as a suction hole by setting a cover to the suction groove and the suction hole opens on the vertical plane in the above configuration.

Moreover, a chip-component carrying system of the present invention is characterized in that many of the suction holes are arranged in the circumferential direction of the vertical plane so that a plurality of suction holes face one chip component.

Furthermore, to solve the above problems, a chip-component visual inspection method of the present invention is characterized by imaging the upside of a chip component by first imaging means and one lateral of the chip component by second imaging means while carrying the chip component by the first rotary disc, and imaging the downside of the chip component by third imaging means, and the other lateral of the chip component by fourth imaging means while carrying the chip component by the second rotary disc.

Furthermore, a chip-component visual inspection system of the present invention is characterized in that the system is provided with the above chip-component carrying system, first imaging means for imaging the upside of a chip component and second imaging means for imaging one lateral of the chip component while carrying the chip component by the first rotary disc and third imaging means for imaging the downside of the chip component and fourth imaging means for imaging the other lateral of the chip component while carrying the chip component by the second rotary disc.

Furthermore, to solve the above problems, a chip component carrying method of the present invention is characterized by suction-holding a chip component on a vertical plane of a second rotary disc and carrying the chip component and then supporting the chip component by a first rotary disc on a horizontal plane and carrying it.

Furthermore, a chip-component carrying method of the present invention is characterized by suction-holding a chip component on the outer periphery of a second rotary disc rotating in a vertical plane and carrying the chip component and then suction-holding the chip component on a one-side vertical plane of a first rotary disc rotating in a vertical plane and carrying it.

Furthermore, a chip-component carrying method of the present invention is characterized in that the first and second rotary discs continuously rotate in the above configuration.

Furthermore, a chip-component carrying method of the present invention is characterized by using a centering roller inscribed with the carrying route of a chip component carried by the first rotary disc at the inner periphery side of the carrying route and thereby adjusting the circumferential speed of the centering roller to the circumferential speed of the first rotary disc at a position inscribed with the carrying route to reform the attitude of the chip component contacting with the outer periphery of the centering roller so as to approach the chip component to the tangent direction of the carrying route in the above configuration.

Furthermore, a chip-component carrying system of the present invention is characterized by including a second rotary disc for suction-holding a chip component on a vertical plane and carrying it and a first rotary disc for supporting the chip component carried by the second rotary disc on a horizontal plane and carrying it.

Furthermore, a chip-component carrying system of the present invention is characterized by including a second rotary disc which rotates in a vertical plane to suction-hold a chip component on the outer periphery and carries it and a first rotary disc which rotates in a vertical plane to suction-hold the chip component on a one-side vertical plane and carries it.

Furthermore, a chip-component carrying system of the present invention is characterized in that the system is provided with a centering roller inscribed with a carrying route of a chip component carried by the first rotary disc at the inner periphery side of the carrying route in the above configuration and the circumferential speed of the centering roller coincides with the circumferential speed of the first rotary disc at a position inscribed with the carrying route, and the attitude of the chip component contacting with the outer periphery of the centering roller is reformed so as to make the chip component approach to the tangent direction of the carrying route in the above-described configuration.

Furthermore, a chip-component carrying system of the present invention is characterized in that the first rotary disc has a suction-hole forming plate portion on which many suction holes are torically arranged at equal intervals so that a plurality of suction holes face one chip component and a vacuum suction plate portion on which a plurality of vacuum suction grooves are formed so that one vacuum suction groove communicates every suction group constituted of a plurality of suction holes and the suction hole forming plate portion is integrated with the upside of the vacuum suction plate portion in the above configuration.

Furthermore, a chip-component visual inspection method of the present invention is characterized by using the above-described chip-component carrying method and thereby imaging the upside of a chip component by first imaging means and one lateral of the chip component by second imaging means while carrying the chip component by the first rotary disc and imaging the downside of the chip component by third imaging means and other lateral of the chip component by fourth imaging means while carrying the chip component by the second rotary disc.

Furthermore, a chip-component visual inspection method of the present invention is characterized by using the above-described chip-component carrying method and thereby imaging the upside of a chip component by first imaging means, one lateral of the chip component by second imaging means, and the other lateral of the chip component by fourth imaging means while carrying the chip component by the first rotary disc, and imaging the downside of the chip component by third imaging means while carrying the chip component by the second rotary disc.

Furthermore, a chip-component visual inspection method of the present invention is characterized by including the above-described chip-component carrying system, first imaging means for imaging the upside of the chip component and second imaging means for imaging one lateral of the chip component, and third imaging means for imaging the downside of the chip component and fourth imaging means for imaging the other lateral of the chip component while carrying the chip component by the second rotary disc.

Furthermore, a chip-component visual inspection system of the present invention is provided with the above-described chip-component carrying system, first imaging means for imaging the upside of the chip component, second imaging means for imaging one lateral of the chip component, and fourth imaging means for imaging the other lateral of the chip component while carrying the chip component by the first rotary disc, and third imaging means for imaging the downside of the chip component while carrying the chip component by the second rotary disc.

The present invention makes it possible to realize a chip-component carrying method and system for stably carrying a workpiece while stabilizing the attitude by first and second rotary discs, stabilizing the delivery operation according to improvement of the workpiece delivery between rotary discs, and accelerating and stabilizing a series of workpiece carryings by first and second rotary discs.

Furthermore, by using the chip-component carrying method and carrying system, it is possible to realize a chip-component visual inspection method and system capable of improving the number of inspections, decreasing the inspection cost, and improving the inspection accuracy and yield. Particularly, the method and system are effective to improve and stabilize the inspection accuracy in the visual inspection of four sides of very small chip components (1005, 0603, 0402 and so on).

BRIEF DESCRIPTION OF THE DRAWINGS

FIGS. 4A, 4B, 4C, and 4D show a component member of a second rotary disc of the embodiment 1, in which FIG. 4A is a top view of a plate portion provided with a toric groove, FIG. 4B is an enlarged view of the X area on the top view of FIG. 4A on which many very-small suction grooves are radially formed through half etching (shown by hatched portion), FIG. 4C is a top view of a discoid cover plate portion for forming a very small suction hole by setting a cover to the upside of a very-small suction groove, and FIG. 4D is a local side view of a state when forming a very-small suction hole by overlapping a plate portion provided with a toric groove with a discoid cover plate;

FIGS. 10A and 10B show a configuration of a portion for supplying a chip component from a part feeder to a first rotary disc, in which FIG. 10A is a partial-side sectional view before improving a chip-component incident angle and FIG. 10B is a partial-side sectional view before improving a chip-component incident angle in embodiment 2;

FIGS. 11A and 11B show a configuration of a portion for supplying a chip component from a part feeder to a first rotary disc in the embodiment 2, in which FIG. 11A a top view of a guide portion using a lateral of a chute portion and FIG. 11B is a sectional view of the same side;

FIGS. 12A and 12B show another configuration of a portion for supplying a chip component from a part feeder to a first rotary disc in the embodiment 2, in which FIG. 12A is a top view of a configuration in which a separately-attached guide portion is formed at the front end of a chute portion and FIG. 12B is a sectional view of the same side;

FIGS. 13A and 13B show a configuration of a first rotary disc of the embodiment 2, in which FIG. 13A is a front sectional view and FIG. 13B is an enlarged top view;

FIGS. 14A and 14B show a suction-hole forming plate portion constituting the first rotary disc, in which FIG. 14A is a top view and FIG. 14B is a front sectional view;

FIGS. 15A and 15B show a vacuum-suction plate portion constituting the first rotary disc, in which FIG. 15A is a top view and FIG. 15B is a front sectional view;

FIGS. 18A and 18B show a configuration around the second rotary disc of the embodiment 4, in which FIG. 18A is a schematic block diagram of a portion for supplying a chip component from a part feeder to the second rotary disc and FIG. 18B is a schematic block diagram of an actuator for discharging chip components set around the second rotary disc.

BEST MODE FOR CARRYING OUT THE INVENTION

Figure 1:
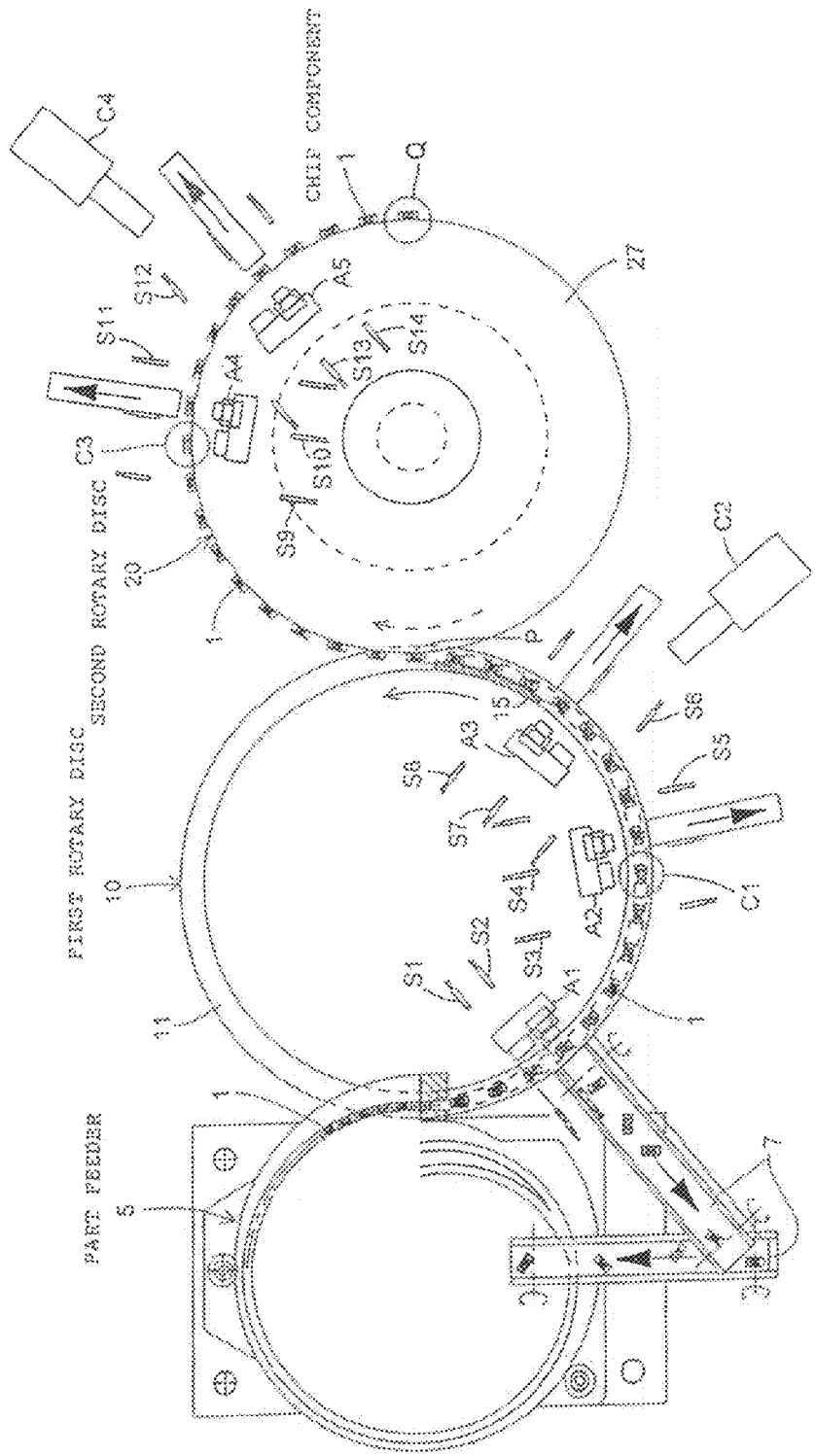
FIG. 1 is a top view showing embodiment 1 of a chip-component carrying method and system and visual inspection method and system of the present invention.

Hereafter, embodiments of a chip-component carrying method and system and a visual inspection method and system are described below as the best mode for carrying out the present invention in accordance with the accompanying drawings.

In FIGS. 1 to 5, embodiments 1 of a chip-component carrying method and system and a visual inspection method and system are described. In these drawings, a rectangular parallelepiped serving as a workpiece is constituted of a first rotary disc 10 and a second rotary disc 20 and a chip component 1 is successively supplied from a part feeder 5 to a chip located plane (upside) 11 of the fringe region of the first rotary disc 10. In this case, the front end of the part feeder 5 is formed into a shape for guiding a lateral of a chip component in order to properly keep the attitude of the chip component 1 when delivering the chip component 1 to the first rotary disc-10 side. However, it is also allowed to form a nonvibrational portion at the front end and form a guide of the chip component.

Figure 2:
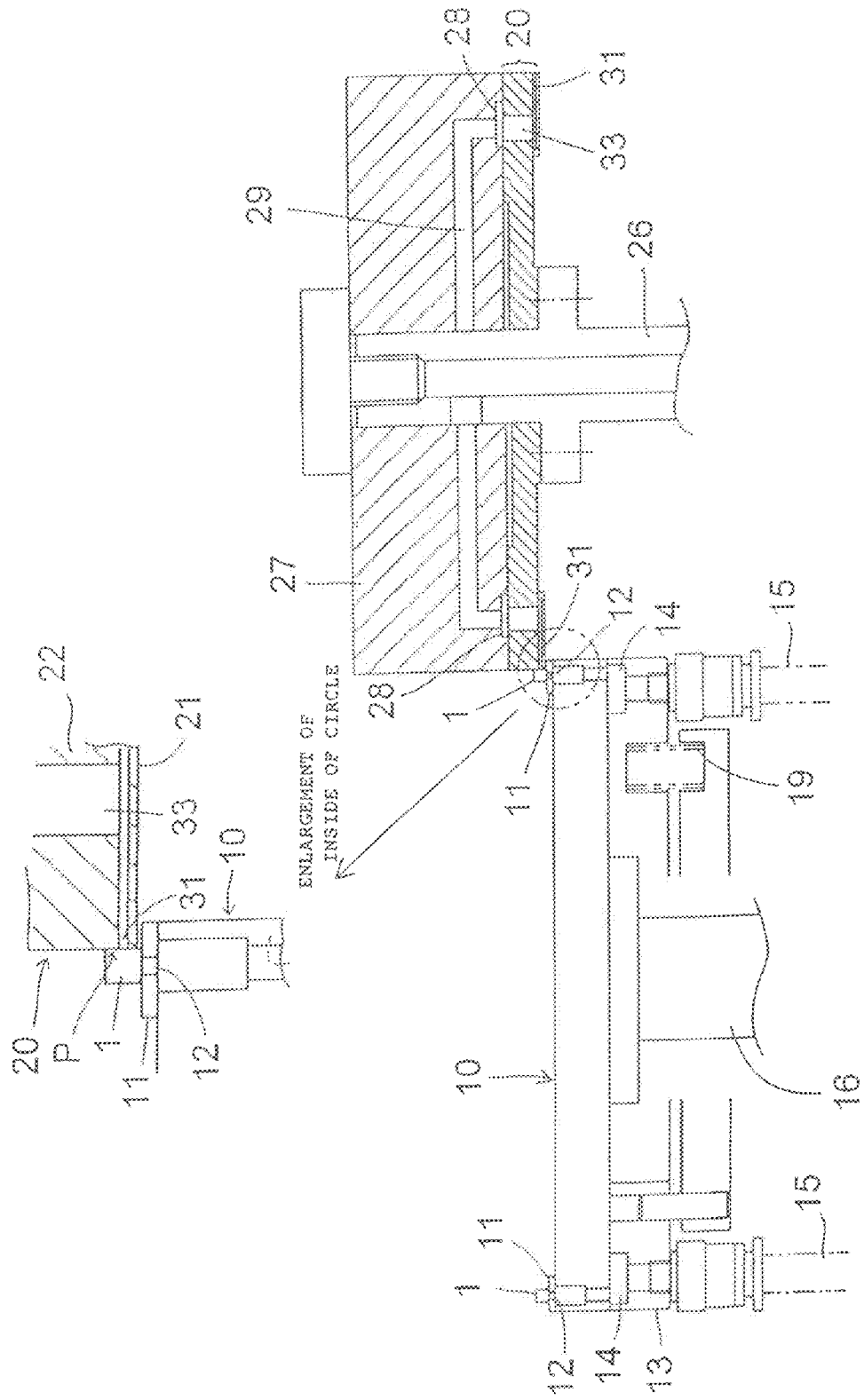
FIG. 2 is a front sectional view of the embodiment 1.
Figure 3:
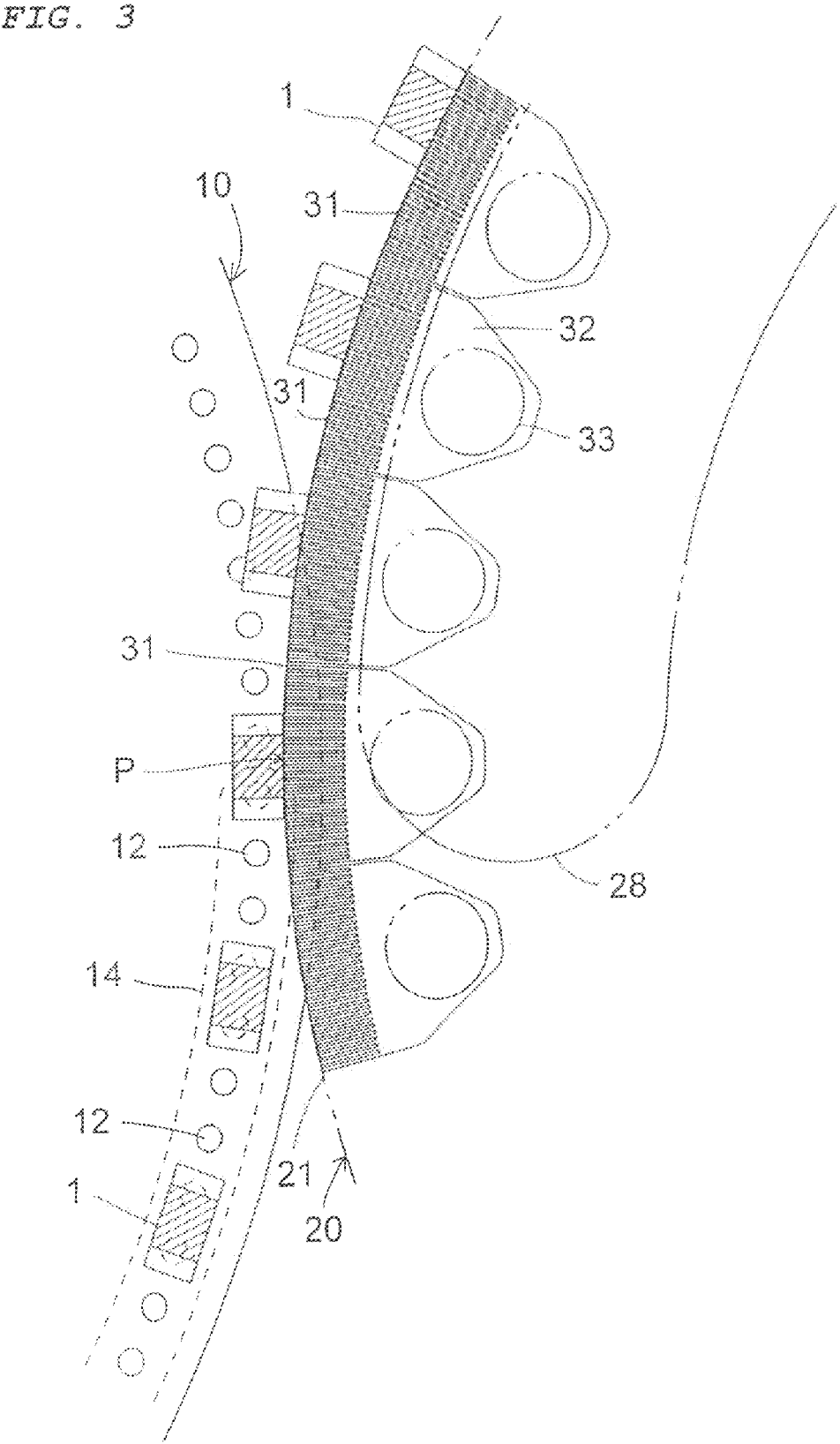
FIG. 3 is an enlarged top sectional view of a delivery portion from a first rotary disc to a second rotary disc in the embodiment 1.
Figure 5:
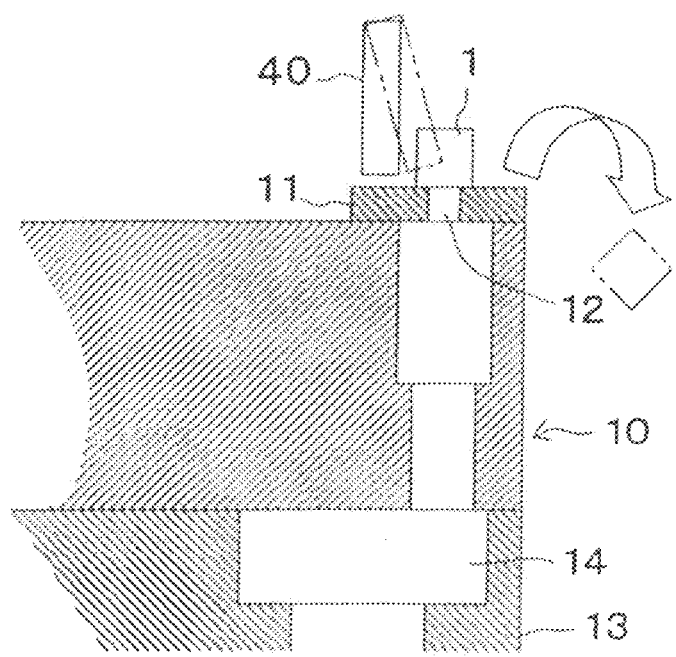
FIG. 5 is a schematic block diagram of an actuator for discharging chip components used for the embodiment 1.

As shown in FIG. 2, the first rotary disc 10 is fixed to a first rotation driving shaft 16 to continuously rotate in accordance with the continuous rotation of the rotation driving shaft 16. As shown in FIGS. 2, 3, and 5, many suction holes 12 are open on the chip located plane 11 of the first rotary disc 10 in order to suction-hold the chip component 1. Moreover, a vacuum exhaust plate 13 which is not rotated closely contacts with the downside of the first rotary disc 10 (energized in the close-contact direction by a spring 19) and a fixed vacuum suction groove 14 is formed on the upside of the vacuum exhaust plate 13. The fixed vacuum suction groove 14 is connected to a vacuum exhaust system such as a vacuum pump through a hose 15. Therefore, the suction holes 12 of the first rotary disc 10-side vacuum-suck the downside of the chip component 1 in a range in which it is communicated with the fixed vacuum suction groove 14. In this case, as shown in FIG. 3, it is preferable that one chip component 1 is vacuum-sucked and held by a plurality of suction holes 12. To decrease leak of vacuum, the forming range of the fixed vacuum suction groove 14 is set so that vacuum suction of the suction holes 12 runs short after the chip component is delivered to the second rotary disc-20 side and until this side of the supply position of the chip component 1 (suction by suction holes 12 is effective in the range of a half round for carrying the chip component 1). A structure is used in which vacuum can be turned on/off depending on the position of the fixed vacuum suction groove formed on the vacuum exhaust plate 13.

The second rotary disc 20 suction-holds the lateral of the rectangular-parallelepiped chip component 1 on the circumferential plane (lateral of outer periphery) constituting the vertical plane, which is fixed to a second rotation-driving shaft 26 and continuously rotates in accordance with the continuous rotation of the rotation-driving shaft 26. The second rotary disc 20 continuously rotates at a circumferential speed almost equal to that of the first rotary disc 10 and rotates in the same moving direction when the chip component 1 is mounted (rotational direction of the second rotary disc 20 is reverse to that of the first rotary disc 10). Moreover, the second rotary disc 20 is present at a position upper than the first rotary disc 10 (there is a gap at upside of first rotary disc and downside of second rotary disc). In the case of planar arrangement, the vertical circumferential plane of the second rotary disc 20 is present at the inside of the external margin of the chip located plane 11 of the first rotary disc 10 (central axis side of first rotary disc), which is a positional relation capable of securely bringing the circumferential plane of the second rotary disc 20 into contact with a lateral of the chip component to transfer it.

Figure 4A:
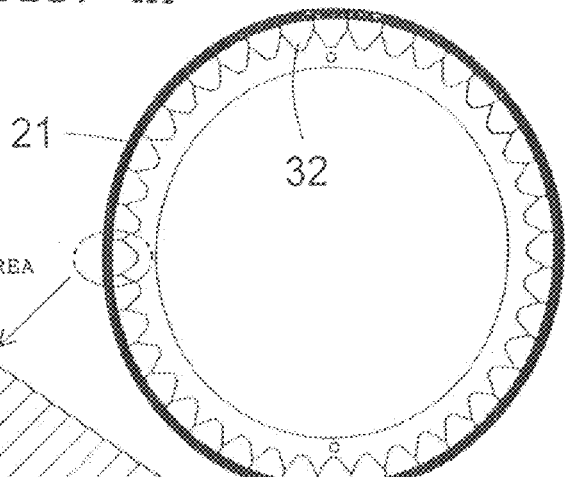
Figure 4B:
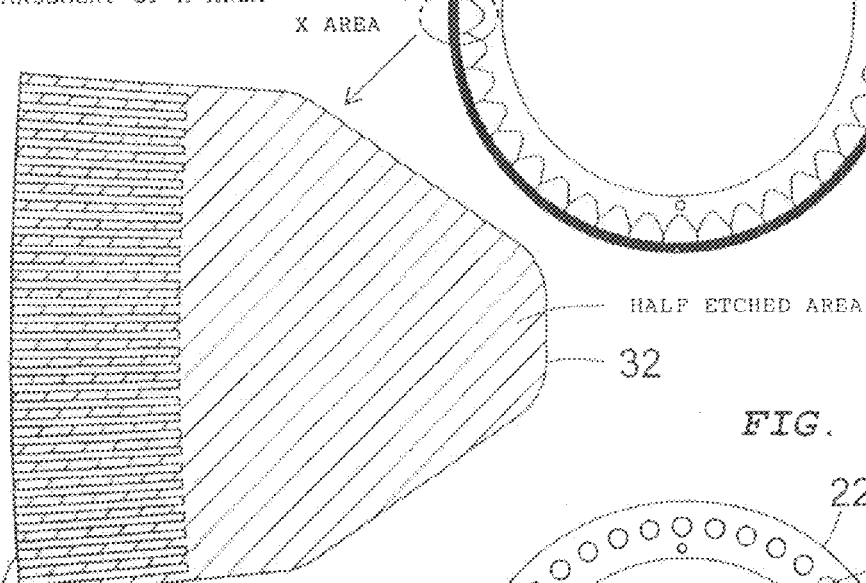
Figure 4C:
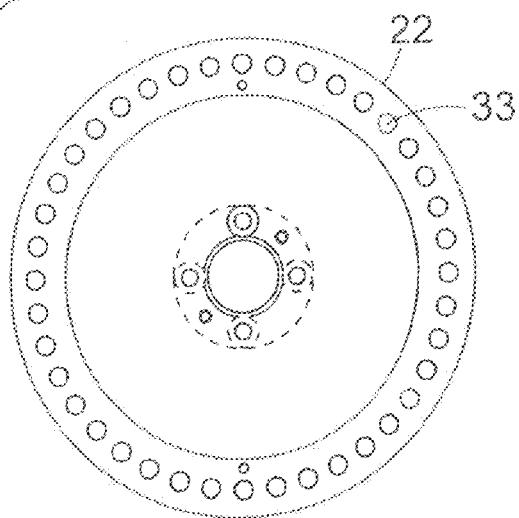
Figure 4D:
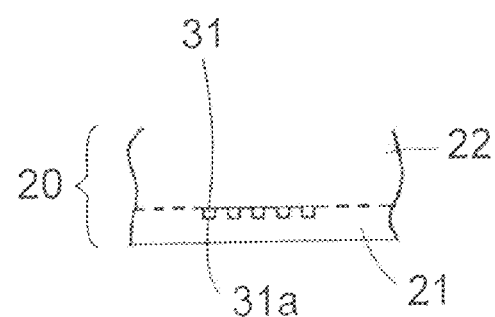

As shown in FIG. 3 and FIGS. 4A and 4B, the second rotary disc 20 has many very-small suction holes 31 opened on the circumferential plane serving as a vertical plane. The central height of each suction hole 31 coincides with the center of the chip-component height on the first rotary disc 10. Moreover, these very-small suction holes 31 are obtained by overlapping the plate portion 21 provided with a toric groove in FIG. 4A on which very-small suction grooves 31a are radially formed through half etching shown by hatched portion in FIG. 4B with a discoid cover plate portion 22 for forming the very-small suction holes 31 by setting a cover to the upside of the very-small suction holes 31a as shown in FIG. 4D and constituting the second rotary disc 20.

As shown in FIGS. 3 and 4B, bases of a group of very-small suction holes 31a communicate with a confluence groove portion 32 and moreover, vacuum suction holes 33 formed on the discoid cover plate portion 22 respectively communicate with the confluence groove portion 32.

A vacuum exhaust plate 27 which does not rotate closely contacts with the upside of the second rotary disc 20 and a fixed vacuum suction groove 28 is formed on the downside of the disc 20 over a half round. Therefore, the vacuum suction holes 33 at the discoid cover plate-22 side are connected to a vacuum exhaust system such as a vacuum pump through the fixed vacuum suction groove 28 at the vacuum exhaust plate-27 side and a vacuum suction route 29 communicating with the groove 28. Thereby, the very-small suction holes 31 opening on the vertical circumferential plane at the second rotary disc-20 side vacuum-suck the chip component 1 in a range in which it is communicated with the fixed vacuum suction groove 28. In this case, as shown in FIG. 3, it is preferable that one chip component 1 is vacuum-sucked and held by many very-small suction holes 31.

In the case of this carrying system, the first rotary disc 10 continuously rotates at a circumferential speed higher than the supply speed of chip components at the part feeder-5 side and separates and carries the chip components 1 in accordance with the speed difference. The chip components 1 supplied to the chip located plane 11 of the first rotary disc 10 are lined up on the circumference and carried by keeping a stable attitude at almost equal intervals because the downsides of the chip components 1 are vacuum-sucked by the suction holes 12 of the first rotary disc 10 and when the chip components 1 go half around, they reach the point P serving as the delivery position to the second rotary disc 20.

As shown in FIG. 1, it is preferable to set a fixed line-up guide 15 at this side of the delivery position and align the traveling position and attitude of the chip components 1 on the first rotary disc 10.

Then, the chip-component-side plane is sucked and held by the second rotary disc 20 by bringing the circumferential plane (outer-periphery lateral) forming the vertical plane of the second rotary disc 20 into contact with the lateral side (outside) of the chip components 1 mounted on the first rotary disc 10.

In this case, fixed vacuum suction grooves 14 and 28 are formed on the vacuum exhaust plates 13 and 27 corresponding to the first and second rotary discs 10 and 20 so that suction at the first rotary disc-10 side becomes turned-off at the contact point P and circumferential-plane suction of the second rotary disc 20 become turned-on at this side of the contact point.

The chip components 1 on the first rotary disc 10 most-closely approach the second rotary disc 20 at the contact point P (resultantly, contacts with the disc 20) and then, slowly separate from the second rotary disc 20. Therefore, it is preferable that vacuum suction at the first rotary disc-10 side becomes vacuum-turned-off nearby the contact point P. Moreover, because the second rotary disc 20 contacts with the chip components 1 at the contact point P, it is preferable that vacuum suction is effective before the contact point P in view of suction stability (vacuum suction becomes an overlapped state nearby the contact point).

Thus, the chip components 1 are continuously transferred from the first rotary disc 10 to the second rotary disc 20 while the attitude of a chip component is stabilized. Therefore, the chip components 1 are not damaged because an extra force equal to or more than a vacuum suction force is not applied to the chip components 1.

When the chip components 1 transferred to the second rotary disc 20 are vacuum-sucked and held by the very-small suction holes 31 at laterals of the chip components 1 and carried over a half round, and the vacuum suction of the very-small suction holes 31 is turned off (fixed vacuum suction groove 28 is formed for only a half round), the chip components 1 drop from the circumferential plane of the second rotary disc 20 and are collected.

Then, a configuration for performing the visual inspection of a chip component by using the above carrying system is described below.

First camera C1 and second camera C2 serving as imaging means are arranged by facing the carrying route of the chip components 1 on the first rotary disc 10 and third camera C3 and fourth camera C4 are arranged by facing the carrying route of the chip components 1 on the second rotary disc 20. The first camera C1 images and inspects (image processing inspection) the upside of the chip components 1 and the second camera C2 images and inspects one lateral of the chip components 1, the third camera C3 images and inspects the downside of the chip components 1, and the fourth camera C4 images and inspects other lateral of the chip components 1, which are, for example, CCD cameras or line sensors.

Moreover, first to eighth workpiece detecting sensors S1 to S8 are fixed along the carrying route of the chip components 1 on the first rotary disc 10. Furthermore, ninth to fourteenth workpiece detecting sensors S9 to S14 are fixed along the carrying route of the chip components 1 on the second rotary disc 20. Each of the sensors S1 to S14 is an optical sensor in which the light emitting side and the light receiving side are paired. The sensors S9 to S14 corresponding to the second rotary disc 20 are schematically illustrated like horizontal arrangement in FIG. 1. However, because the chip component 1 is sucked to the vertical circumferential plane of the second rotary disc 20 and carried, the sensors S9 to S14 are actually arranged in the vertical direction.

Furthermore, because the chip components 1 are discharged in accordance with a sensor detection result or imaging or inspection result of each camera, first to third actuators A1 to A3 are arranged correspondingly to the carrying route of the chip components 1 on the first rotary disc 10 and fourth and fifth actuators A4 and A5 are arranged correspondingly to the carrying route of the chip components 1 on the second rotary disc 10. As shown in FIG. 5, each of the actuators A1 to A5 uses a chip-component discharge mechanism 40 or the like using a piezoelectric element in order to realize the discharge operation of, for example, a very-small workpiece. The actuators A4 and A5 respectively have a configuration for dropping a chip component sucked by the vertical circumferential plane of the second rotary disc 20 downward.

Third, sixth, ninth and twelfth workpiece detecting sensors S3, S6, S9, and S12 set to this side of the first to fourth cameras C1 to C4 respectively generate a trigger signal for imaging continuous carrying objects. Moreover, second, fourth, seventh, tenth, and thirteenth workpiece detecting sensors S2, S4, S7, S10, and S13 set to this side of the first to fifth actuators A1 to A5 respectively generate a trigger signal for the workpiece discharge operation.

In the case of this embodiment, the general operation for performing visual inspection of a chip component is described below.

As shown in FIG. 1, chip components 1 serving as workpieces are successively supplied from the front end of the part feeder 5 to the chip located plane 11 (upside) on the fringe of the first rotary disc 10. The first rotary disc 10 continuously rotates at a circumferential speed higher than the supply speed of a chip component at the part feeder-5 side. Therefore, chip components 1 are separated in accordance with the speed difference and carried. The chip components 1 supplied to the chip located plane 11 of the first rotary disc 10 are lined up on the circumference and carried in almost equal intervals while keeping a stable attitude because the downsides of the chip components 1 are vacuum-sucked by the suction holes 12 of the first rotary disc 10.

Then, when the chip component 1 passes before the first and second workpiece detecting sensors S1 and S2, a set of the first and second workpiece detecting sensors S1 and S2 detect that passed chip components are not lined up (incorrect pitch) to operate the first actuator A1 and returns unlined-up chip components 1 to a part feeder 5 through an unlined-up part collecting portion 7. The unlined-up part collecting portion 7 is a belt conveyer or the like.

The lined-up chip components 1 passing through a portion before the first actuator A1 are detected by the third workpiece detecting sensor S3 (to continuously image carried objects, a trigger signal for imaging the objects by the sensor before a camera is generated) and then upsides of the chip components 1 are imaged and inspected (image processing inspection) by the first camera C1 and a chip component failing in the inspection is discharged by the second actuator A2 after passing of the chip component is detected by the fourth workpiece detecting sensor S4 (trigger signal for discharging chip component by sensor before actuator is generated). The fifth workpiece detecting sensor S5 is used to confirm discharge.

The chip component 1 whose upside is inspected is passing-detected by the sixth workpiece detecting sensor S6 and then, one lateral of the chip component 1 is imaged and inspected by the second camera C2, and a chip component failing in the inspection is discharged by the third actuator A3 after the chip component is passing-detected by the seventh workpiece detecting sensor S7. The eighth workpiece detecting sensor S8 is used to confirm discharge.

The chip component 1 passing through a portion before the third actuator A3 is guided by the fixed line-up guide 15 so that the go-around radius and attitude of the chip component 1 become proper and as shown by an enlargement view in FIG. 3, reaches the contact point P to the second rotary disc 20.

At the contact point P for delivering a chip component, vacuum suction of the suction holes 12 at the upside of the first rotary disc 10 and vacuum suction of the suction holes 31 at the lateral of the second rotary disc 20 are turned on and the lateral of the chip component 1 contacting with the vertical plane of the second rotary disc 20 is sucked and held at the second rotary disc-20 side. Thereafter, as the chip component 1 moves, the vacuum suction of the suction holes 12 at the first rotary disc-10 side is turned off. Therefore, the chip component 1 is carried in accordance with continuous rotation of the second rotary disc 20.

Then, the chip components 1 transferred to the second rotary disc 20 are passing-detected by the ninth workpiece detecting sensor S9, the downsides of them are imaged and inspected by the third camera C3, and a chip component failing in the inspection is passing-detected by a tenth workpiece detecting sensor S10 and then discharged by the fourth actuator A4. An eleventh workpiece detecting sensor S11 is used to confirm discharge.

The chip component 1 whose downside is inspected is passing-detected by a twelfth workpiece detecting sensor S12 and then, the other lateral of the component 1 is imaged and inspected by the fourth camera C4, and a chip component failing in the inspection is passing-detected by a thirteenth workpiece detecting sensor S13 and then discharged by the fifth actuator A5. A fourteenth workpiece detecting sensor S14 is used to confirm discharge. Then, the nondefective chip component 1 whose upside, one lateral, downside, and the other lateral are inspected reaches a nondefective discharge position Q and at this position, the chip component 1 is discharged and collected because vacuum suction of the suction holes 31 of the second rotary disc 20 is turned off.

According to this embodiment 1, it is possible to obtain the following advantages.

Figure 6:
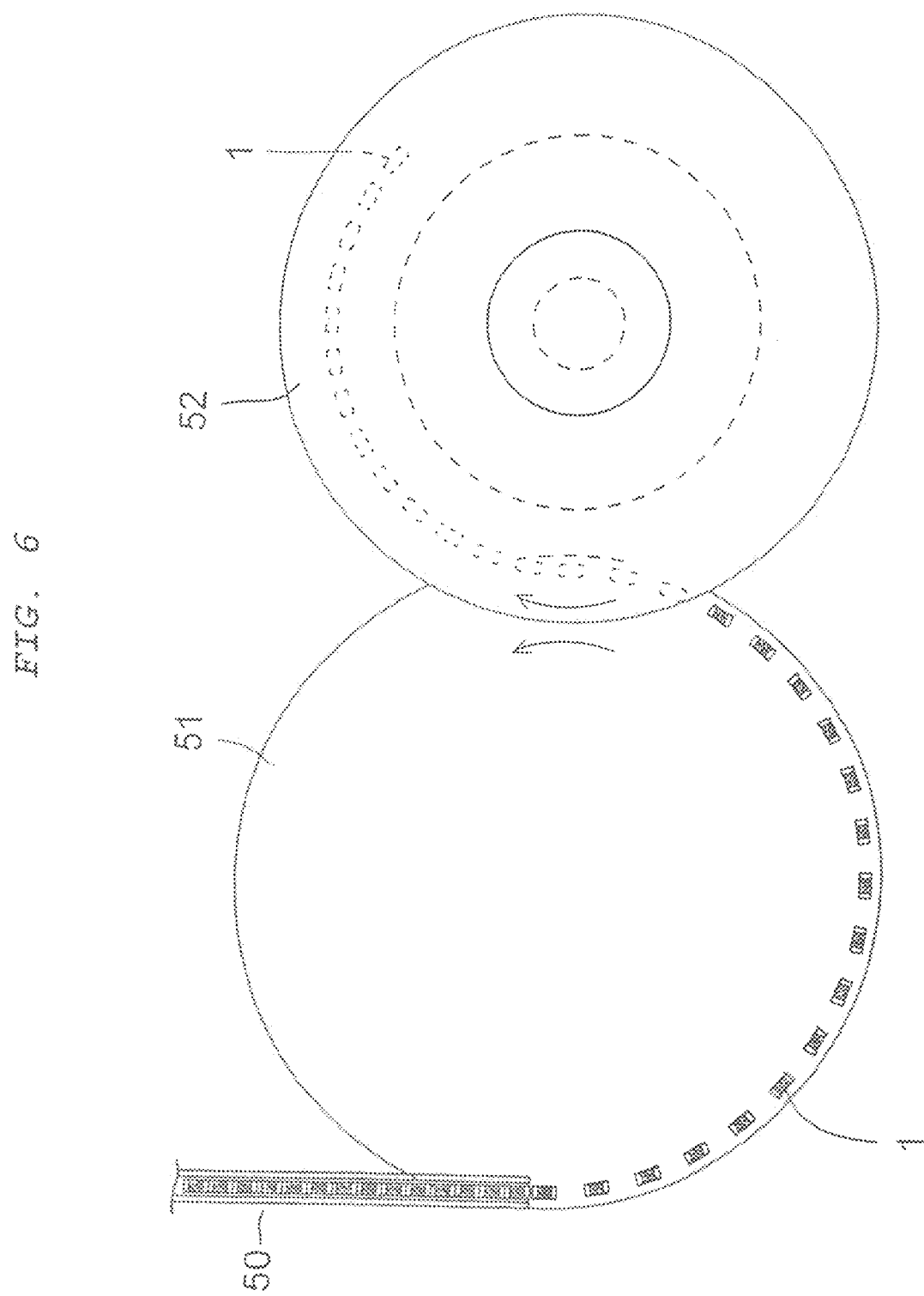
FIG. 6 is a top view showing a conventional carrying system.
Figure 7:
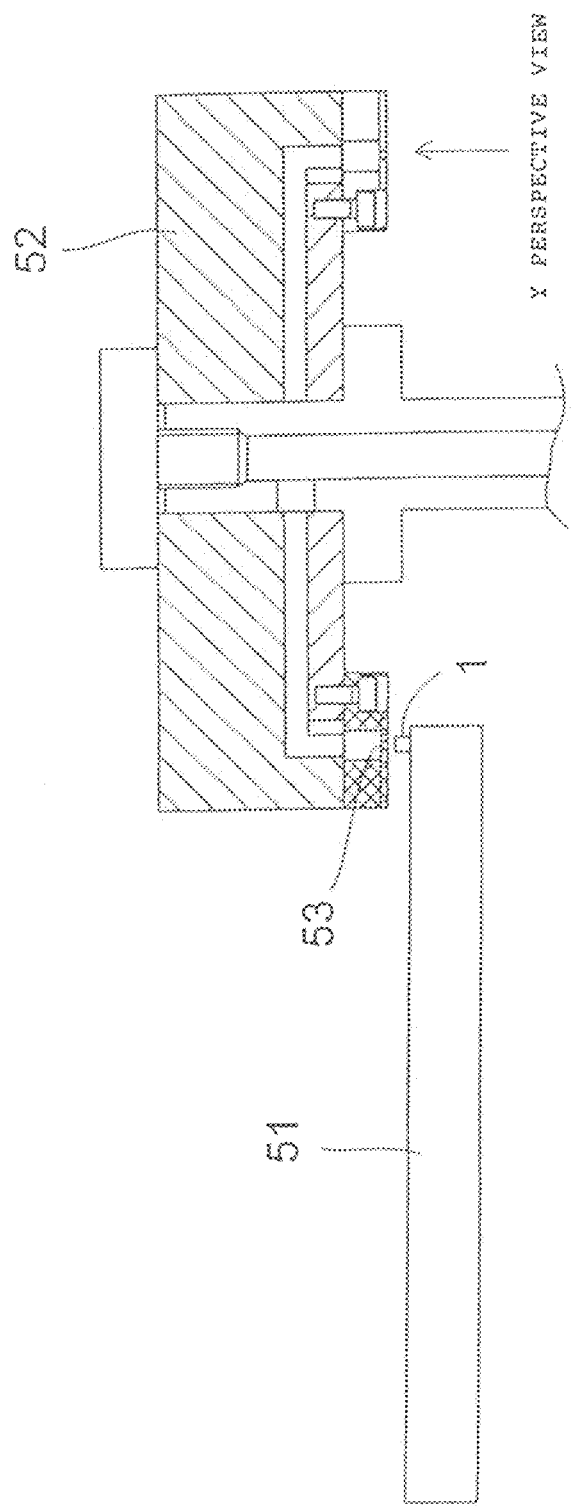
FIG. 7 is a front sectional view of the conventional carrying system.
Figure 8:
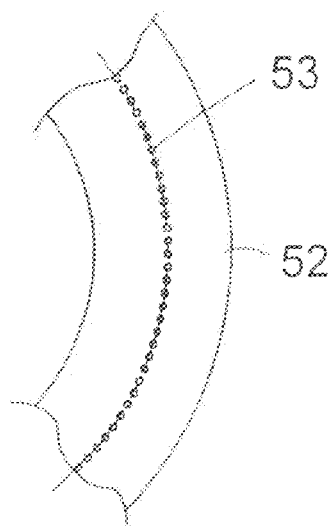
FIG. 8 is a Y perspective view of FIG. 7.

(1) Because a configuration is used in which the chip component 1 serving as a workpiece is sucked and held on a horizontal plane of the first rotary disc 10 and carried and then sucked and held on the vertical plane of the second rotary disc 20 and carried, chip components can be transferred from the first rotary disc 10 to the second rotary disc 20 independently of the fluctuation of the thickness of a chip component, and the chip-component delivery operation is securely performed. A trouble due to the fluctuation of the thicknesses of chip components or breakage of a chip component which occurs in a conventional example as shown in FIGS. 6 and 7 does not occur. Moreover, it is possible to transfer a chip component without changing the attitude of the chip component (without vertically or horizontally reversing the attitude) and stably carry the chip component.

(2) By continuously rotating the first rotary disc 10 and second rotary disc 20 and suction-holding the chip component 1 by the suction holes 12 in the case of the first rotary disc 10 and by the suction holes 31 in the case of the second rotary disc 20 and carrying the chip component, it is possible to accelerate the carrying speed and stabilize the carrying attitude of the chip component.

(3) The second rotary disc 20 is constituted by arranging many very-small suction holes 31 on a circumferential plane forming a vertical plane of the disc 20 in a circumferential direction. Therefore, by sucking the lateral of each chip component 1 by many very-small suction holes 31, it is possible to stably carry the chip component 1 without causing the shift of the carrying attitude of the component 1. Then, by forming the second rotary disc 20 into a structure in which the plate portion 21 provided with a toric groove on which many suction grooves 31a are formed radially through half etching is overlapped with the discoid plate portion 22 by setting a cover on the suction grooves 31 to use them as suction holes 31, it is possible to constitute the second rotary disc 20 in which many very-small suction holes 31 are opened on the circumference by a small number of component members (combination of two plate portions).

(4) According to the above Items (1) to (3), the number of inspections (throughput) for performing visual inspection of four planes (upside, downside, and two laterals) of a chip component is improved (1.3 to 2.0 times larger than the case of conventional example) and the inspection cost can be decreased.

(5) It is expected that the inspection accuracy is improved and the yield in an inspection step is improved. Particularly, in the case of a very-small chip component (1005 type, 0603 type, 0402 type or the like) having a length of 1 mm or less, it is possible to improve and stabilize the inspection accuracy and obtain an inspection method and system having a high reliability. It is preferable to use the above chip component whose thickness and width have an almost equal dimension, in other words, a rectangular-parallelepiped chip component whose cross section is almost close to a square for carrying a condenser, inductor, thermistor, or varistor. A flat chip having a small thickness like a chip resistance is improper.

Embodiment 2 of the present invention is described by referring to FIG. 9 to FIGS. 15A and 15B. In these drawings, the first rotary disc 10 and second rotary disc 20 constitute the carrying system of a rectangular-parallelepiped chip component serving as a workpiece and a configuration in which the chip components 1 are successively supplied to the chip located plane (upside) 11 on the outer margin of the first rotary disc 10 from the part feeder 5 is the same as the case of the embodiment 1.

Figure 10A:
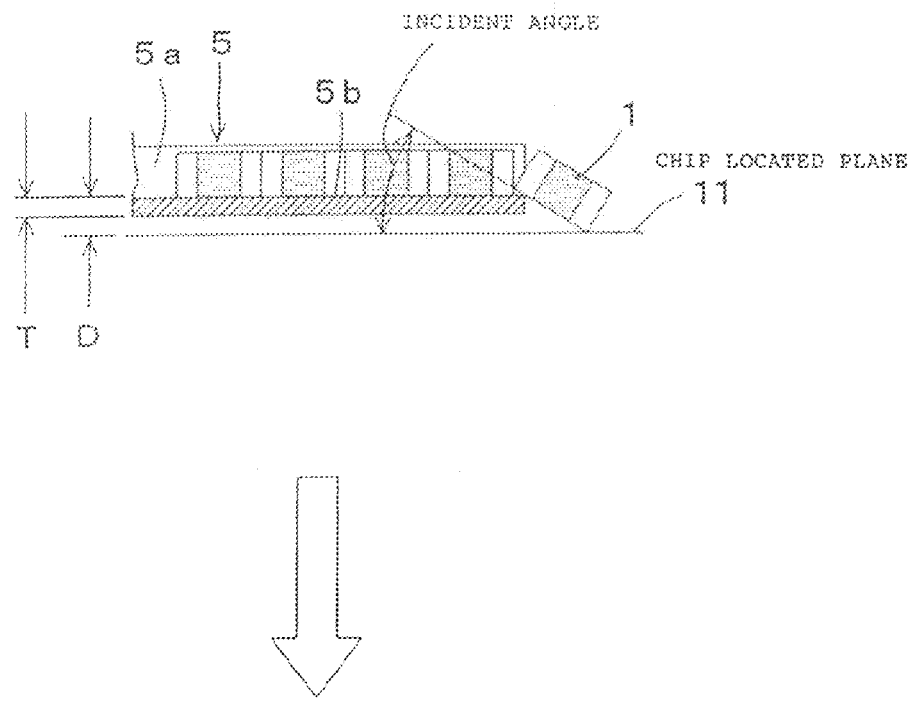
Figure 10B:
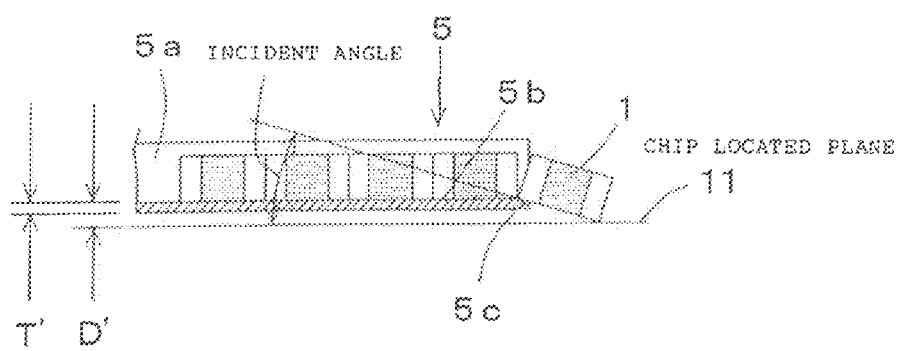

In this case, when supplying a chip component from the part feeder 5 to the first rotary disc 10, the chute portion of the part feeder 5 is set to the upside of the chip located plane 11 of the first rotary disc 10 as shown in FIG. 10. However, a small gap is necessary so that the first rotary disc 10 does not interfere with the chute portion of the part feeder 5. Moreover, when delivering the chip component 1 to the first rotary disc 10, it is necessary to minimize the distance D between the bottom (carrying plane) 5b of a workpiece carrying groove 5a as a chute portion of the part feeder 5 and the chip mounting plane 11 of the first rotary disc 10 because when the distance D is not minimized, the tilt (incident angle) of a chip component at the time of delivery is increased and a problem of incorrect attitude such as standing of the chip component 1 occurs. Therefore, it is necessary to minimize the wall thickness T of the bottom portion of the workpiece carrying groove 5 of the part feeder 5. In the case of the configuration before taking an action in FIG. 10A, because the wall thickness T of the bottom portion of the work carrying groove 5 is not small, the distance D from the chip located plane 11 of the first rotary disc 10 is large and the incident angle becomes excessively large in the case of a minimum-size chip component. However, as shown in FIG. 10B, by setting the wall thickness of the bottom portion of the workpiece carrying groove 5 to a very small value T', the distance from the chip located plane 11 of the first rotary disc 10 is decreased, by forming a slope 5c at the front end of the workpiece carrying groove 5a, the incident angle of a chip component is decreased, and it is possible to stabilize the delivery attitude of the chip component 1 to the chip located plane 11. This effect is remarkable in the case of a minimum-size chip component.

Moreover, when supplying the chip component 1 from the part feeder 5 to the first rotary disc 10, the chute portion of the part feeder 5 has a groove shape for constraining three to four planes of four planes in the longitudinal direction of the chip component 1, that is, a workpiece carrying groove 5a as shown in FIGS. 11A and 11B. However, when a constraint plane is eliminated when the chip component 1 exits from the chute portion and is supplied to the chip located plane 11, the chip component rotates when delivering the chip component to the chip located plane 11 of the first rotary disc 10 and the attitude of the chip component is fluctuated. When the chip-component attitude is fluctuated, the reflection degree of an inspection plane is fluctuated in visual inspection in the back end step. Therefore, this causes deterioration of an inspection accuracy.

To improve the attitude fluctuation of the chip component 1, a configuration is provided using a workpiece-attitude control guide 5d in which both sides of the chute portion are extended from the bottom portion 5b of the chute portion in order to constrain both laterals of the chip component 1 at the position of delivery as shown in FIGS. 11A and 11B or a separately-set workpiece-attitude control guide 5d' is used as shown in FIGS. 12A and 12B.

However, when using the above workpiece-attitude control guides 5d and 5d', it is necessary to consider a workpiece dimension tolerance. For example, in the case of a 0603-size condenser, it is necessary that the width and height of a workpiece are 0.3±0.03 mm, the length is 0.6±0.03 mm, and guide width is 0.33 mm or more. In fact, by considering a maximum dimension, it is necessary to consider the guide width as 0.35 mm. When considering a workpiece having the minimum tolerance, a maximum gap of 0.08 mm occurs and a maximum tilt of 7.6° occurs in the length of the workpiece of 0.6 mm.

According to an experimental result, it is found that the tilt of a chip component allowable for visual inspection is kept within ±6°. When the tilt exceeds ±6°, fluctuation occurs in defect extraction of a chip component because reflected light changes.

Figure 9:
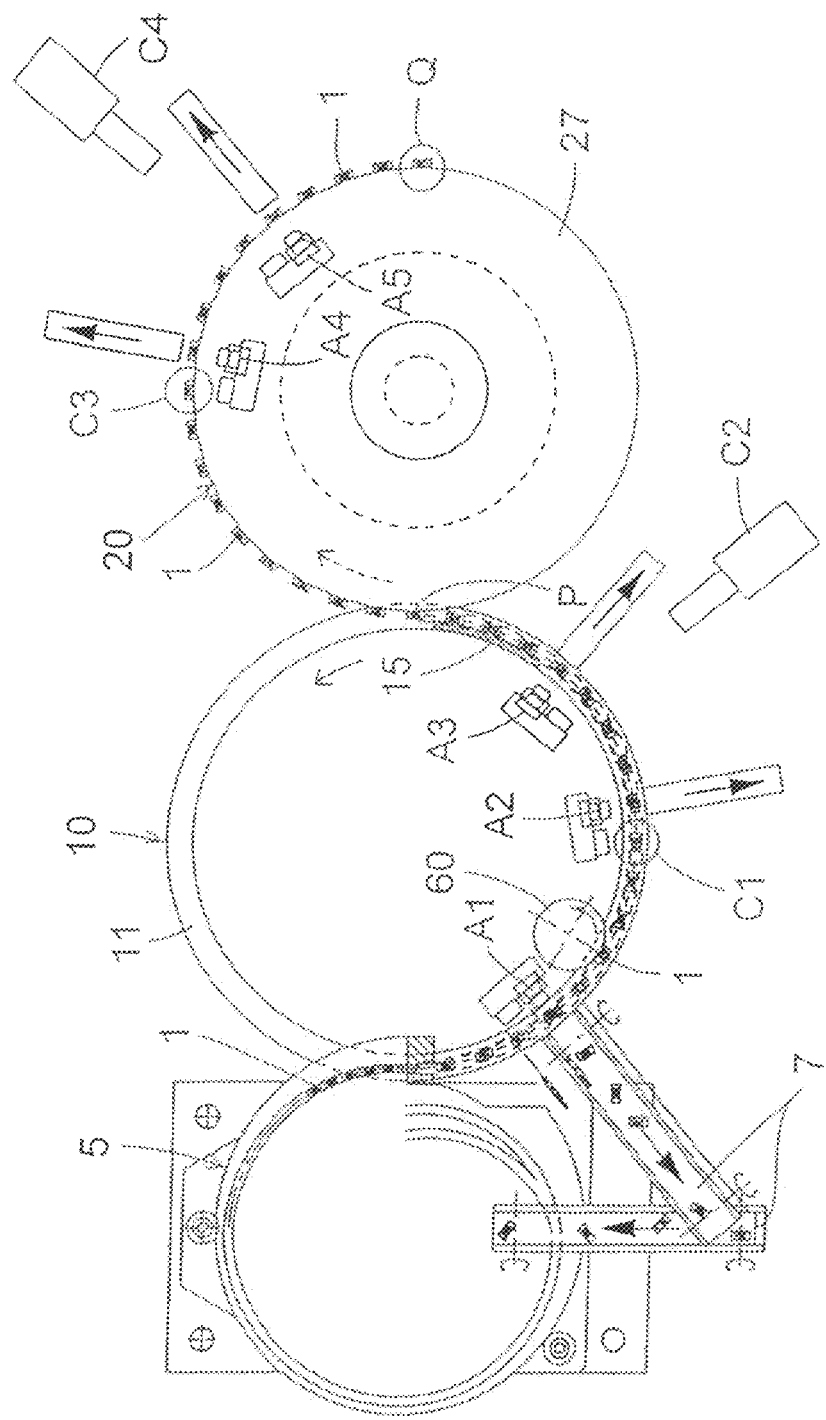
FIG. 9 is a top view showing embodiment 2 of the present invention.

Therefore, only the above workpiece attitude control guides 5d and 5d' shown in FIGS. 11A and 11B and FIGS. 12A and 12B are insufficient for visual inspection. Therefore, as shown in FIG. 9, a centering roller 60 serving as an attitude reforming portion for further performing the attitude reformation of a chip component at a stage before visual inspection is set above the first rotary disc 10. In this case, the centering roller 60 continuously rotates so that the outer periphery of a carrying route is inscribed with a carrying route at the inner periphery side of the toric carrying route of the chip component 1 carried by the first rotary disc 10, the circumferential speed of the centering roller 60 coincides with the circumferential speed of the first rotary disc 10 at a position inscribed with the carrying route (coincides with the circumferential speed of the inner lateral of the chip component moving through the carrying route), and attitude reformation is performed so as to make the attitude of the chip component 1 contacting with the outer periphery of the centering roller 60 approach to the tangent direction of the carrying route.

Thus, by making the circumferential speed of the centering roller 60 continuously rotating above the first rotary disc 10 coincide with the circumferential speed of a chip component, deterioration of a chip-component attitude due to friction resistance at the time of contact or contact resistance with the centering roller 60 is moderated, and it is possible to perform attitude reformation of a chip component serving as a mobile body being continuously carried at a high speed.

By keeping the attitude of the chip component 1 in a constant fluctuation range by the workpiece attitude control guides 5d and 5d' at the front end of the chute portion of the part feeder 5 and further performing high-accuracy attitude reformation by the centering roller 60, it is possible to keep the attitude of the chip component within ±5° (within 4σ, σ: standard deviation).

Moreover, the first rotary disc 10 is described below. When supplying a workpiece to a continuously-rotating suction disc, supply of workpieces is irregular. Therefore, it is difficult to control the positional relation between a suction hole and a workpiece. Thus, a porous suction disc is used and it is possible to suction-hold a workpiece independently of the workpiece and suction hole positions. However, like the case of each embodiment of the present invention, when delivering a chip component serving as a workpiece between two suction discs, a porous disc cannot smoothly perform vacuum change or delivery of a workpiece is not stabilized (because of porous state, surrounding region becomes vacuum state, vacuum state is not turned off at the time of delivery of workpiece and thereby delivery operation is not stabilized).

Figure 13A:
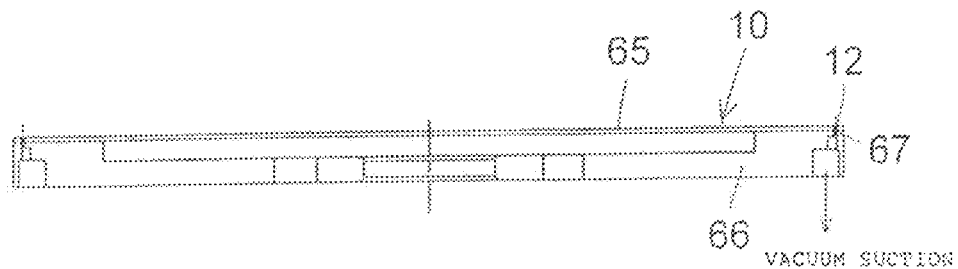
Figure 13B:
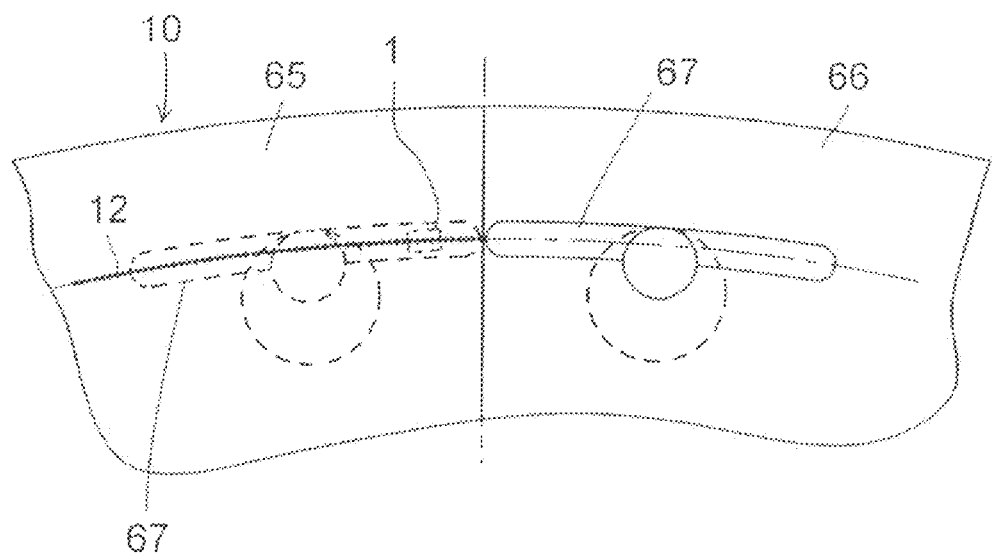

Therefore, in the case of this embodiment, the first rotary disc 10 has the structure shown in FIGS. 13A and 13B to FIGS. 15A and 15B. That is, the first rotary disc 10 has a suction-hole forming plate portion 65 on which many suction holes 12 are torically arranged at equal intervals so that a plurality of suction holes 12 shown in FIGS. 14A and 14B face (open to) one chip component 1 and a vacuum suction plate portion 66 on which a plurality of vacuum suction grooves 67 are separately formed like an island every suction hole group constituted of a plurality of suction holes 12 so that the vacuum suction grooves 67 in FIGS. 15A and 15B are communicated by corresponding to each other and the suction-hole forming plate portion 65 are integrated on the vacuum suction plate portion 66 as shown in FIGS. 13A and 13B. As shown in FIG. 2 of the embodiment 1, a not-rotated vacuum exhaust plate 13 closely contacts with the downside of the first rotary disc 10 and the vacuum suction grooves 67 communicating with the fixed vacuum suction groove 14 are vacuum-sucked.

As an equal-pitch suction hole forming method to the suction hole forming plate portion 65, etching or laser working is used for a stainless steel plate. Particularly, when a workpiece size is the 0402 size or the like, it is preferable that a suction hole diameter is 0.1 mm or less but the fluctuation of hole diameters increases for etching. Moreover, in the case of etching, a workable hole diameter and plate thickness of stainless steel are restricted (generally, because up to one-to-one correspondence of workable hole diameter and plate thickness is limited, there are problems that plate thickness of stainless steel is 0.1 mm or less) and it is difficult to obtain the rigidity of stainless steel. Therefore, to form a suction hole, it is preferable to apply laser working using UV-YAG laser or femto-second laser to a stainless-steel plate and in this case, it is possible to realize a plate thickness of 0.3 mm.

As seen from FIG. 13B, by forming many very-small suction holes 12 on the circumference passing through the center of a chip-component carrying route at equal intervals in order to suction-hold a chip component on the vacuum suction plate portion 66 provided with vacuum suction grove 67 formed like an island, it is possible to suction-hold the chip component independently of a chip-component supply position, perform communication (on) and cut-off (off) of vacuum suction every vacuum suction groove 67 formed like an island, and stably perform chip-component delivery when continuously carrying the chip components 1.

Other configuration of the embodiment 2 is the same as that of the above-described embodiment 1 and the same or a corresponding portion is provided with the same symbol and its description is omitted.

Figure 16:
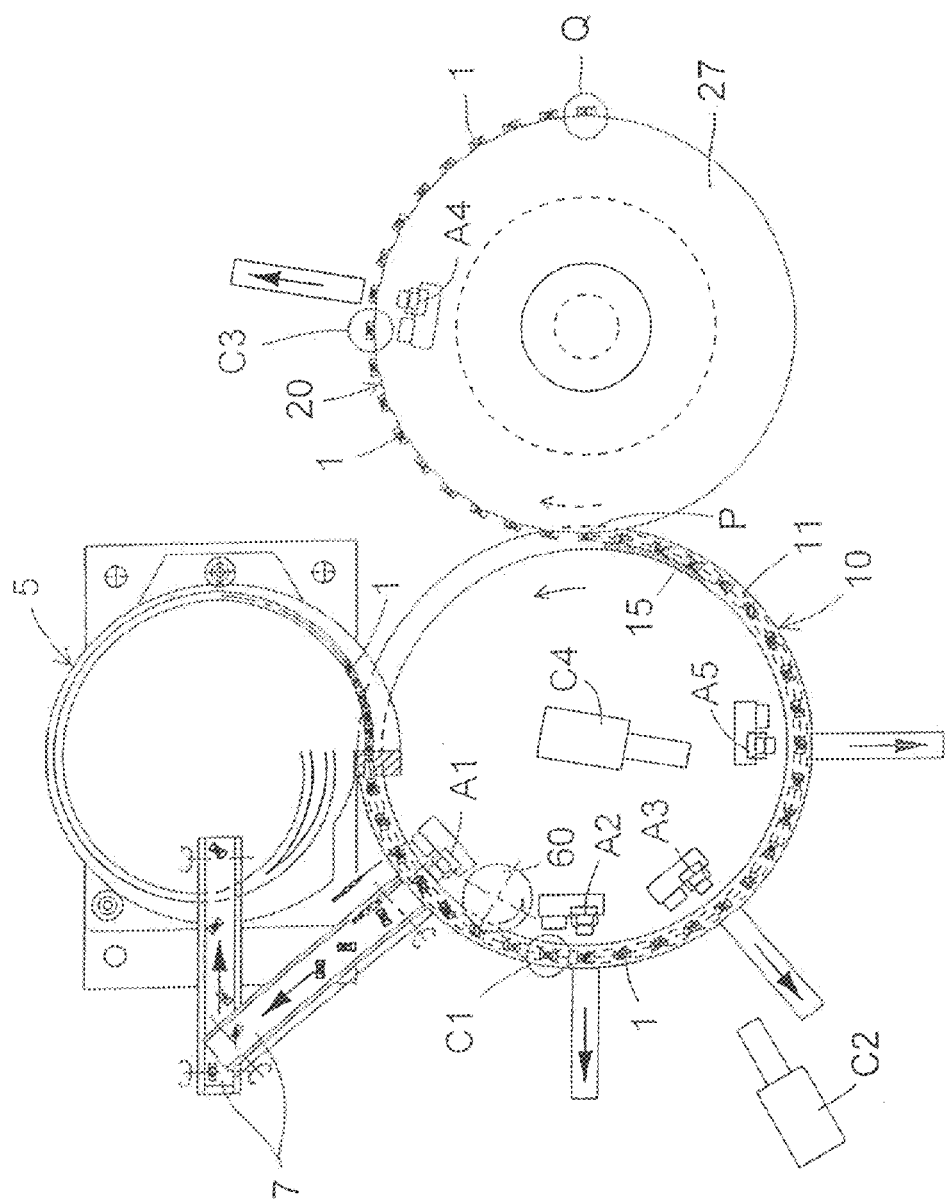
FIG. 16 is a top view showing third embodiment of the present invention.

FIG. 16 shows embodiment 3 of the present invention, in which the arrangement of a camera serving as imaging means for performing visual inspection is changed. In this case, first camera C1, second camera C2 and fourth camera C4 serving as imaging means are arranged by facing the carrying route of the chip component 1 of the first rotary disc 10 and third camera C3 is set by facing the carrying route of the chip component 1 of the second rotary disc 20. The first camera C1 corresponding to the carrying route of the first rotary disc 10 images and inspects (image processing inspection) the upside of the chip component 1, second camera C2 images and inspects one lateral of the chip component 1, fourth camera C4 images and inspects the other lateral of the chip component 1, and third camera C3 corresponding to the carrying route of the second rotary disc 20 images and inspects the downside of the chip component 1, which are CCD cameras or line sensors. In this case, a chip component is carried by approx. ¾ rounds by the first rotary disc 10 so that three cameras can be arranged.

Other configuration of the embodiment 3 is the same as the configuration of the embodiment 1 or 2 and the same or corresponding portion is provided with the same symbol and description of it is omitted.

Figure 17:
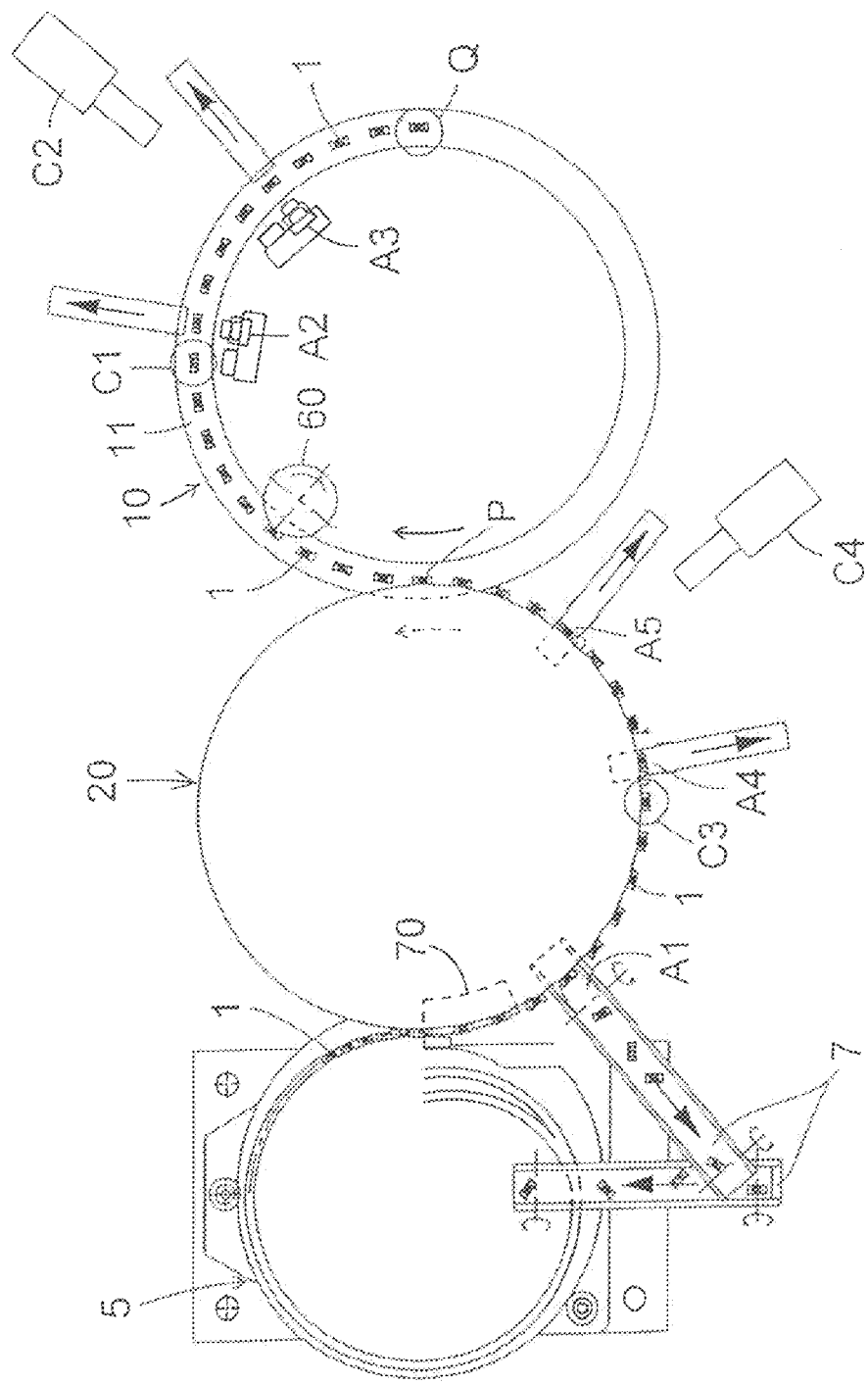
FIG. 17 is a top view sowing embodiment 4 of the present invention.

FIG. 17 shows embodiment 4 of the present invention, which is the same as the embodiments 1, 2, and 3 in that the first rotary disc 10 and second rotary disc 20 are used to carry chip components and shows a configuration in which the order for carrying chip components is replaced.

Figure 18A:
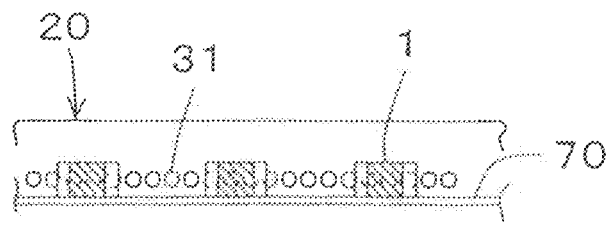
Figure 18B:
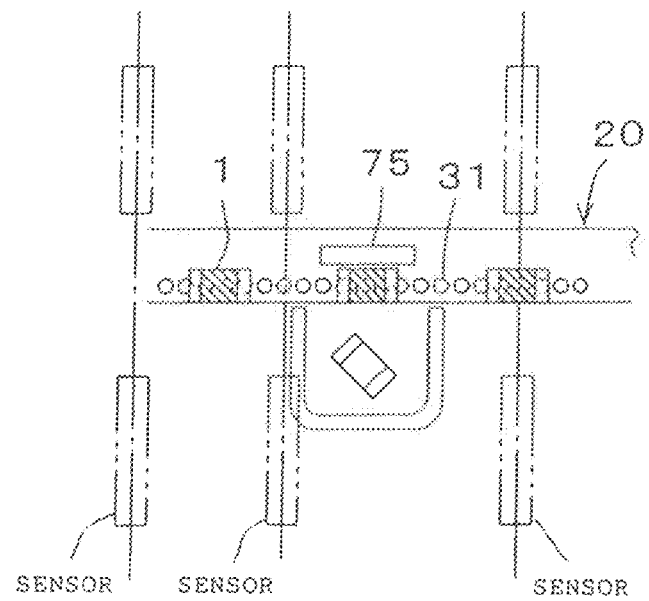

That is, chip components 1 are successively supplied from the part feeder 5 so as to contact with the circumferential plane (outer-periphery lateral) in which the chip component 1 forms the vertical plane of the second rotary disc 20. As shown in FIGS. 18A and 18B, because the second rotary disc 20 has very-small suction holes 31 on the circumferential plane, the chip component 1 is thereby held by vacuum suction, carried over half round, and then delivered to the chip located plane (upside) 11 at the fringe portion of the first rotary disc 10 by turn-off of the vacuum suction.

The chip component 1 transferred to the first rotary disc 10 is held by very-small suction holes of the chip located plane 11 through vacuum suction and carried over half round.

As shown in FIG. 18A, a catching portion 70 having a plane for supporting the chip component 1 at a predetermined height is formed at a position for supplying the chip component 1 from the part feeder 5 to the circumferential plane of the second rotary disc 20 and when the second rotary disc 20 continuously rotates at a circumferential speed faster than the supply speed of chip components at the part feeder-5 side, it is possible to separate and carry the chip components 1 in accordance with the speed difference.

FIG. 18B shows examples of the first, fourth, and fifth actuators A1, A4, and A5 of the embodiment 4. In the case of the first actuator A1, an unlined-up (incorrect pitch) chip component is dropped and discharged and in the case of the fourth and fifth actuators A4 and A5, an imperfect-appearance chip component is dropped and discharged with a piazo actuator 75 using a piezoelectric element. A workpiece detecting sensor is set before and after each actuator (sensor function is the same as that described for embodiment 1).

Other configuration of the embodiment 4 is the same as that of the embodiment 1 or 2 and the same or corresponding portion is provided with the same symbol and its description is omitted.

General operation for performing visual inspection of a chip component in the embodiment 4 is described.

As shown in FIG. 17, chip components 1 serving as workpieces are successively supplied from the front end of the part feeder 5 so as to contact with the circumferential plane (outer periphery) of the second rotary disc 20. Because the second rotary disc 20 continuously rotates at a circumferential speed higher than the supply speed of chip components at the part feeder-5 side, it separates the chip components 1 in accordance with the speed difference and carries them. The chip component 1 supplied so as to contact with the circumferential plane of the second rotary disc 20 are lined up and carried at almost equal intervals while keeping a stable attitude because one lateral of the chip component 1 is vacuum-sucked by the suction holes 31 of the second rotary disc 20.

Then, when there is an unlined-up (imperfect pitch) chip component 1 when passing through the first actuator A1, this is returned to the part feeder 5 through an unlined-up component collecting portion 7. The unlined-up component collecting portion 7 is a belt conveyer or the like.

Downsides of the lined-up chip components 1 passing through the first actuator A1 are imaged and inspected by the third camera C3 and a chip component failing in the inspection is discharged by the fourth actuator A4.

In the chip components 1 whose downsides are inspected, one laterals of them are imaged and inspected by the fourth camera C4 and a chip component failing in the inspection is discharged by the fifth actuator A5.

At the point P for delivering chip components from the second rotary disc 20 to the first rotary disc 10, vacuum suction of the suction holes 12 at the upside of the first rotary disc 10 and vacuum suction of the suction holes 31 at the lateral of the second rotary disc 20 are turned on and the bottom of the chip component 1 contacting with the horizontal plane of the first rotary disc 10 is sucked and the chip component 1 is held at the first rotary disc-10 side. Thereafter, vacuum suction of the suction holes 31 at the second rotary disc-20 side is turned off in accordance with movement of the chip component 1. Therefore, the chip component 1 is carried in accordance with continuous rotation of the first rotary disc 10.

Then, the upside of the chip component 1 is imaged and inspected by the first camera C1 (image processing inspection) and a chip component failing in the inspection is discharged by the second actuator A2. In the chip component 1 whose upside is inspected, remaining one side is image and inspected by the second camera C2 and a chip component failing in the inspection is discharged by the third actuator A3. Then, the nondefective chip component 1 whose downside, one lateral, upside, and the other lateral are inspected reaches the nondefective discharge position Q and here, vacuum suction of the first rotary disc 10 is turned off and thereby, the chip component 1 is discharged and collected by not-illustrated collecting means.

In the case of the embodiment 4, the first rotary disc 10 is located under the second rotary disc 20 to suction-support the bottom of a chip component by the first rotary disc 10 to carry the chip component. However, it is also possible to use a configuration in which the first rotary disc 10 is set above the second rotary disc 20, suction holes 12 are opened downward, and the upside of a chip component is suction-supported by the first rotary disc 10 to carry the chip component.

In the case of the above embodiments 1 to 4, the first rotary disc 10 and second rotary disc 20 continuously rotate in a horizontal plane. However, embodiment 5 having a configuration in which the first rotary disc 10 and second rotary disc 20 continuously rotate in a vertical plane is described by referring to FIG. 19.

Figure 19:
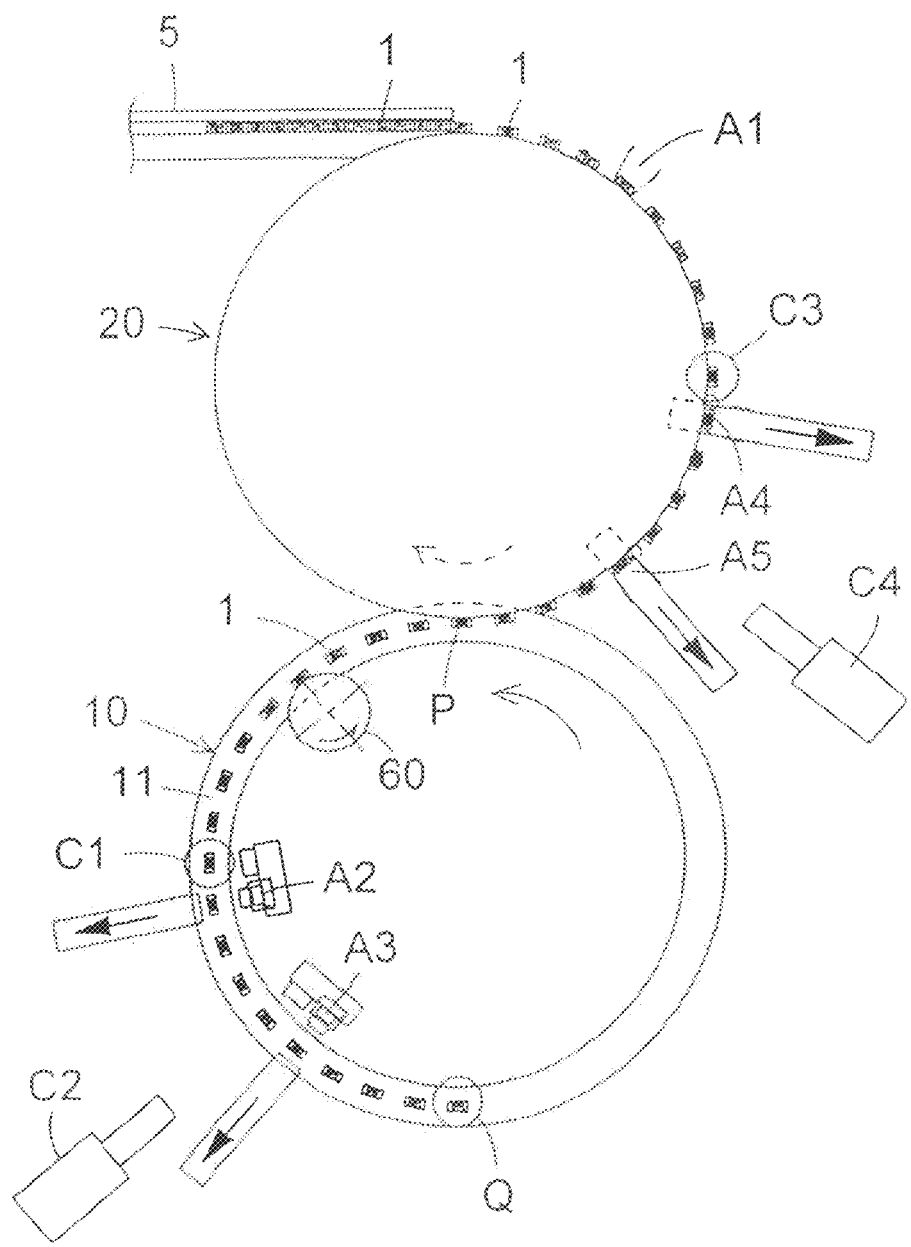
FIG. 19 is a side view showing embodiment 5 of the present invention.

In the case of the embodiment 5 in FIG. 19, the second rotary disc 20 rotates in a vertical plane and suction-holds a chip component on the circumferential plane (outer periphery) on which suction holes are opened to carry the chip component and supplies the chip component 1 from the part feeder 5 onto the circumferential plane. The first rotary disc 10 rotates in a vertical plane, receives a chip component from the second rotary disc 20 at the point P, and suction-holds the chip component on a one-side vertical plane on which suction holes are opened to carry the chip component.

The embodiment 5 is the substantially same as the above-described embodiment 4 in configuration and operation except that the first rotary disc 10 and second rotary disc 20 continuously rotate in a vertical plane and the same or corresponding portion is provided with the same symbol and its description is omitted.

The carrying system of chip components in each of the above embodiments can be used for visual inspection of a chip component and moreover, can be also applied to a measuring instrument other than the visual inspection.

Moreover, each of the above embodiments uses an actuator using a piezoelectric element as a chip-component discharge mechanism. However, as a defective chip-component discharging method, it is possible to use a configuration using blowoff by air.

Furthermore, the camera arrangement of the embodiment 3 shown in FIG. 16 can be applied to the case of embodiment 4 or 5. It is also allowed to use a configuration for imaging the bottom of a chip component at the second rotary disc side by one camera and imaging remaining three planes by three cameras at the first rotary disc side.

Embodiments of the present invention are described above. However, the present invention is not restricted to these embodiments. It is self-evident for those skilled in the art that the present invention can be variously deformed or modified in a range of claims.

This application insists on the priority since Japanese Patent Application No. 2004-117651 applied on Apr. 13, 2004 and its content is cited as a part of this application.

The invention claimed is:

1. A chip component carrying method for carrying a chip component by using a first rotary disc that rotates on a horizontal plane and a second rotary disc that rotates on the horizontal plane in a direction opposite to a rotational direction of the first rotary disc,
   a part of a circumferential surface of the second rotary disc being positioned between on outer edge of a chip mounting surface on the horizontal plane of the first rotary disc and an axis of the first rotary disc,
   a gap between the part of the circumferential surface of the second rotary disc and the chip mounting surface of the first rotary disc being narrower than a height of a chip component, the method comprising:
   carrying the chip component by the rotation of the first rotary disc while holding the chip component by the chip mounting surface of the first rotary disc;
   abutting the chip component to a part of the circumferential surface of the second rotary disc, at a time when the chip component is positioned between the axis of the first rotary disc and an outer periphery of the chip mounting surface of the first rotary disc;
   suctioning and holding the chip component by the circumferential surface of the second rotary disc; and
   carrying the chip component carried by the rotation of the second rotary disc.

2. The chip component carrying method according to claim 1, wherein the first rotary disc and the second rotary disc continuously rotate.

3. A chip component visual inspection method using the chip component carrying method of claim 1 or 2 and thereby, imaging an upside of a chip component by first imaging means and one lateral of the chip component by second imaging means while carrying the chip component by the first rotary disc and imaging a downside of the chip component by third imaging means and the other lateral of the chip component by fourth imaging means while carrying the chip component by the second rotary disc.

4. A chip component carrying method for carrying a chip component by using a first rotary disc that rotates on a horizontal plane and a second rotary disc that rotates on the horizontal plane in a direction opposite to a rotational direction of the first rotary disc,
   a part of a circumferential surface of the second rotary disc being positioned between on outer edge of a chip mounting surface on the horizontal plane of the first rotary disc and an axis of the first rotary disc,
   a gap between the part of the circumferential surface of the second rotary disc and the chip mounting surface of the first rotary disc being narrower than a height of a chip component, the method comprising:
   carrying the chip component by the rotation of the second rotary disc while holding the chip component by the circumferential surface of the second rotary disc;
   transferring the chip component from the circumferential surface of the second rotary disc to the chip mounting surface of the first rotary disc at a time when a part of the circumferential surface of the second rotary disc, suctioning and holding the chip component to come to a position between the axis of the first rotary disc and an outer periphery of the chip mounting surface of the first rotary disc; and
   carrying the chip component carried by the rotation of the first rotary disc while supporting the chip component by the chip mounting surface of the first rotary disc.

5. A chip component carrying method for carrying a chip component by using a first rotary disc that rotates on a vertical plane and a second rotary disc that rotates on the vertical plane in a direction opposite to a rotational direction of the first rotary disc,
   a part of a periphery surface of the second rotary disc being positioned between an outer edge of a chip mounting surface on the vertical plane of the first rotary disc and an axis of the first rotary disc,
   a gap between the part of the periphery surface of the second rotary disc and the chip mounting surface of the first rotary disc being narrower than a height of a chip component, the method comprising:
   carrying the chip component by the rotation of the second rotary disc while holding the chip component by the periphery surface of the second rotary disc;
   transferring the chip component from the periphery surface of the second rotary disc to the chip mounting surface of the first rotary disc at a time when a part of the periphery surface of the second rotary disc, suctioning and holding the chip component to come to a position between the axis of the first rotary disc and an outer periphery of the chip mounting surface of the first rotary disc; and carrying the chip component carried by the rotation of the first rotary disc while suctioning and holding the chip component by the chip mounting surface of the first rotary disc.

6. The chip component carrying method according to claim 4 or 5, wherein the first rotary disc and the second rotary disc continuously rotate.

7. The chip component carrying method according to claim 1, 2, 4, or 5, wherein a centering roller inscribed with a carrying route of a chip component carried by the first rotary disc at the inner periphery side of the carrying route is used, thereby making the circumferential speed of the outer periphery of the centering roller coincide with the circumferential speed of the first rotary disc at a position inscribed with the carrying route, and reforming an attitude of the chip component contacting with the outer periphery of the centering roller so as to make the attitude approach to the tangent direction of the carrying route.

8. A chip component visual inspection method using the chip component carrying method of claim 4 or 5 and thereby imaging an upside of the chip component by first imaging means and one lateral of the chip component by second imaging means while carrying the chip component by the first rotary disc, and imaging a downside of the chip component by third imaging means and the other lateral of the chip component by fourth imaging means while carrying the chip component by the second rotary disc.

9. A chip component visual inspection method using the chip component carrying method of claim 1, 2, 4, or 5 and thereby imaging an upside of a chip component by first imaging means and one lateral of the chip component by second imaging means, and the other lateral of the chip component by fourth imaging means while carrying the chip component by the first rotary disc, and imaging a downside of the chip component by third imaging means while carrying the chip component by the second rotary disc.

* * * * *